US012528782B2

(12) United States Patent
Moslin et al.

(10) Patent No.: US 12,528,782 B2

(45) Date of Patent: Jan. 20, 2026

(54) PRODRUGS IN THE MODULATION OF INTERLEUKIN

(71) Applicant: BRISTOL-MYERS SQUIBB COMPANY, Princeton, NJ (US)

(72) Inventors: Ryan M. Moslin, Princeton, NJ (US); David S. Weinstein, San Diego, CA (US); Thangeswaran Ramar, Hosur (IN); Murugaiah Andappan Murugaiah Subbaiah, Hosur (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 1040 days.

(21) Appl. No.: 17/627,169

(22) PCT Filed: Jul. 14, 2020

(86) PCT No.: PCT/US2020/041876

§ 371 (c)(1),
(2) Date: Jan. 14, 2022

(87) PCT Pub. No.: WO2021/011513

PCT Pub. Date: Jan. 21, 2021

(65) Prior Publication Data

US 2023/0167082 A1 Jun. 1, 2023

Related U.S. Application Data

(60) Provisional application No. 62/874,531, filed on Jul. 16, 2019.

(51) Int. Cl.

| | |
|---|---|
| ***C07D 401/12*** | (2006.01) |
| ***C07D 401/14*** | (2006.01) |
| ***C07D 403/12*** | (2006.01) |

(52) U.S. Cl.

CPC ......... *C07D 401/12* (2013.01); *C07D 401/14* (2013.01); *C07D 403/12* (2013.01)

(58) Field of Classification Search

CPC ... C07D 401/12; C07D 401/14; C07D 403/12
See application file for complete search history.

(56) References Cited

U.S. PATENT DOCUMENTS

| | | | |
|---|---|---|---|
| 9,505,748 | B2 | 11/2016 | Moslin et al. |
| 9,663,467 | B2 | 5/2017 | Moslin et al. |

FOREIGN PATENT DOCUMENTS

| | | | |
|---|---|---|---|
| WO | 2014/074661 | A1 | 5/2014 |
| WO | 2015/069310 | A1 | 5/2015 |
| WO | 2015153304 | A1 | 10/2015 |
| WO | 2018213426 | A1 | 11/2018 |
| WO | 20086616 | A1 | 4/2020 |

*Primary Examiner* — Brian E McDowell

(74) *Attorney, Agent, or Firm* — Jing G. Sun

(57) ABSTRACT

There are disclosed prodrugs of the compounds of the formula. The prodrugs are useful in the modulation of IL-12, IL-23 and/or IFN$\alpha$, by acting on Tyk-2 to cause signal transduction inhibition.

6 Claims, 1 Drawing Sheet

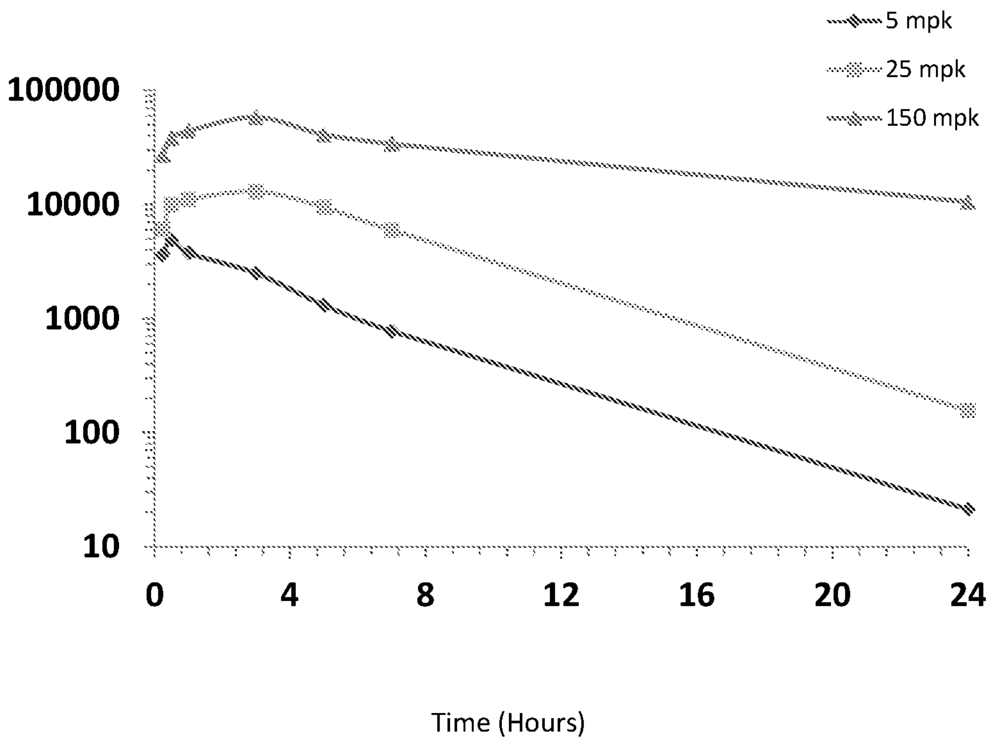
5 mpk
25 mpk
150 mpk
100000
10000
1000
100
10
0
4
8
12
16
20
24
Time (Hours)

PRODRUGS IN THE MODULATION OF INTERLEUKIN

CROSS-REFERENCE TO RELATED APPLICATIONS

This application claims the benefit of U.S. Provisional Application No. 62/874,531, filed Jul. 16, 2019, the disclosure of which is incorporated herein by reference in its entirety.

FIELD OF THE INVENTION

This invention relates to compounds useful as prodrugs in the modulation of IL-12, IL-23 and/or IFNα by acting on Tyk-2 to cause signal transduction inhibition. Provided herein are prodrugs of amide-substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12RB1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.,* 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", *Eur. J. Immunol.,* 26:1217-1221 (1996); Schroder, K. et al., "Interferon-gamma: an overview of signals, mechanisms and functions", *J. Leukoc. Biol.,* 75 (2): 163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.,* 184:4605-4609 (2010); Hong, K. et al., "IL-12, independently of IFN-gamma, plays a crucial role in the pathogenesis of a murine psoriasis like skin disorder", *J. Immunol.,* 162:7480-7491 (1999); Hue, S. et al., "Interleukin-23 drives innate and T cell-mediated intestinal inflammation", *J. Exp. Med.,* 203:2473-2483 (2006); Cua, D. J. et al., "Interleukin-23 rather than interleukin-12 is the critical cytokine for autoimmune inflammation of the brain", *Nature,* 421:744-748 (2003); Murphy, C. A. et al., "Divergent pro- and anti-inflammatory roles for IL-23 and IL-12 in joint autoimmune inflammation", *J. Exp. Med.,* 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.,* 199:125-130 (2004); Tzartos, J. S. et al., "Interleukin-17 production in central nervous system infiltrating T cells and glial cells is associated with active disease in multiple sclerosis", *Am. J. Pathol.,* 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.,* 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.,* 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut,* 60:1739-1753 (2011); Tao, J. H. et al., "Meta-analysis of TYK2 gene polymorphisms association with susceptibility to autoimmune and inflammatory diseases", *Mol. Biol. Rep.,* 38:4663-4672 (2011); Cho, J. H. et al., "Recent insights into the genetics of inflammatory bowel disease", *Gastroenterology,* 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet,* 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology,* 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet,* 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.,* 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.,* 197:711-723 (2003); Peterson, K. S. et al., "Characterization of heterogeneity in the molecular pathogenesis of lupus nephritis from transcriptional profiles of laser-captured glomeruli", *J. Clin. Invest.,* 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus,* 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.,* 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.,* 6:683-692 (2010); Sandling, J. K. et al., "A candidate gene study of the type I interferon pathway implicates IKBKE and IL8 as risk loci for SLE", *Eur. J. Hum. Genet.,* 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.,* 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.,* 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.,* 187:181-189 (2011); Prchal-Murphy, M. et al., "TYK2 kinase activity is required for functional type I interferon responses in vivo", *PLOS One,* 7: e39141 (2012)) and humans (Minegishi, Y. et al., "Human tyrosine kinase 2 deficiency reveals its requisite roles in multiple cytokine signals involved in innate and acquired immunity", *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.,* 187:181-189 (2011); Oyamada, A. et al., "Tyrosine kinase 2 plays critical roles in the pathogenic CD4 T cell responses for the development of experimental autoimmune encephalomyelitis", *J. Immunol.,* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain,* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.,* 90:636-647 (2012); Graham, D. et al., "Association of polymorphisms across the tyrosine kinase gene, TYK2 in UK SLE families", *Rheumatology* (*Oxford*), 46:927-930 (2007); Eyre, S. et al., "High-density genetic mapping identifies new susceptibility loci for rheumatoid arthritis", *Nat. Genet.,* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

U.S. Pat. No. 9,663,467 discloses compounds useful for treating diseases and conditions related to the modulation of IL-12, IL-23 and/or IFNα such as autoimmune and inflammatory diseases. This reference is assigned to the present assignee and is incorporated herein by reference in its entirety.

The compound shown below which is disclosed therein (I)

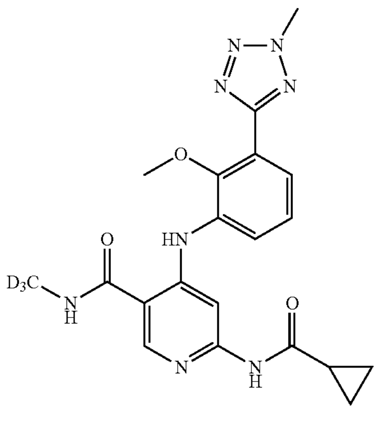

has shown activity against the targets.

U.S. Pat. No. 9,505,748 also discloses compounds useful for treating diseases and conditions related to the modulation of IL-12, IL-23 and/or IFNα such as autoimmune and inflammatory diseases. This reference is assigned to the present assignee and is incorporated herein by reference in its entirety.

The compound shown below which is disclosed therein (II)

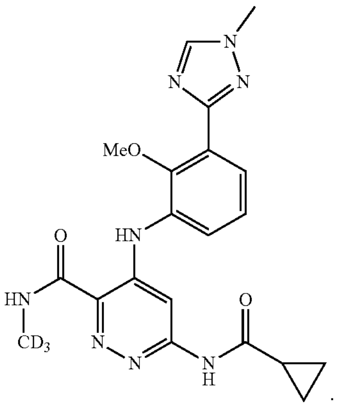

has shown activity against the targets.

As may be appreciated, there remains a need for improved delivery of the above compounds to the patient.

Applicants have found prodrugs of Compounds (I) and (II) useful for the administration of Compounds (I) and (II), respectively. The prodrugs have better solubility at physiological important pH values than Compounds (I) and (II), and surprisingly allow the administration of Compounds (I) and (II) with a wider dosage range and/or a broader range of pharmaceutical formulations. These prodrug compounds are provided to be useful as pharmaceuticals with desirable stability, bioavailability, therapeutic index, and toxicity values that are important to their drugability.

SUMMARY OF THE INVENTION

The invention is directed to prodrugs of Compounds (I) and (II) which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

BRIEF DESCRIPTION OF THE DRAWINGS

The invention is illustrated by reference to the accompanying drawings described below.

FIG. 1 shows the PK of a prodrug of Compound I. The rats were dosed PO at the following dosages using the following symbols: (◇)—5mpk, (□)—25 mpk and (◇)—150 mpk. Maximum observed circulating prodrug was <0.05% of parent (150 mpk dose).

DETAILED DESCRIPTION OF THE EMBODIMENTS OF THE INVENTION

The first aspect of the invention provides prodrugs of Compounds (I) and (II) as shown below (I)

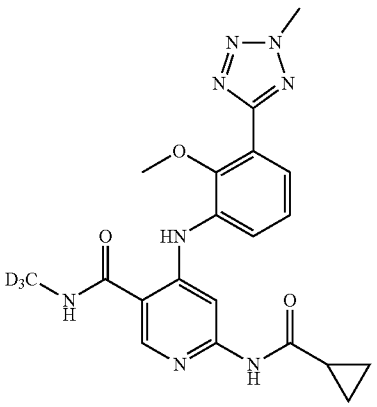

and (II)

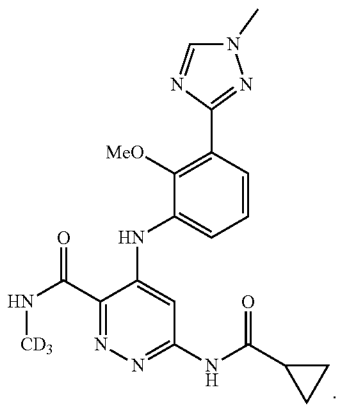

In a second aspect of the invention, there are provided the following compounds of the invention:
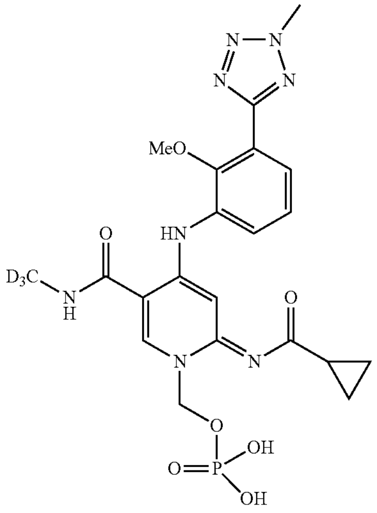 [SMILES: [2H]C([2H])([2H])NC(=O)c1cn(COP(=O)(O)O)/c(=N/C(=O)C2CC2)cc1Nc1cccc(-c2nnn(C)n2)c1OC]
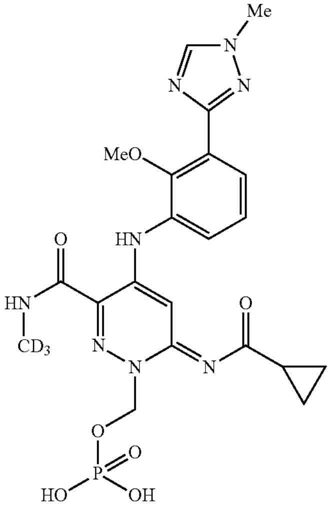
-continued
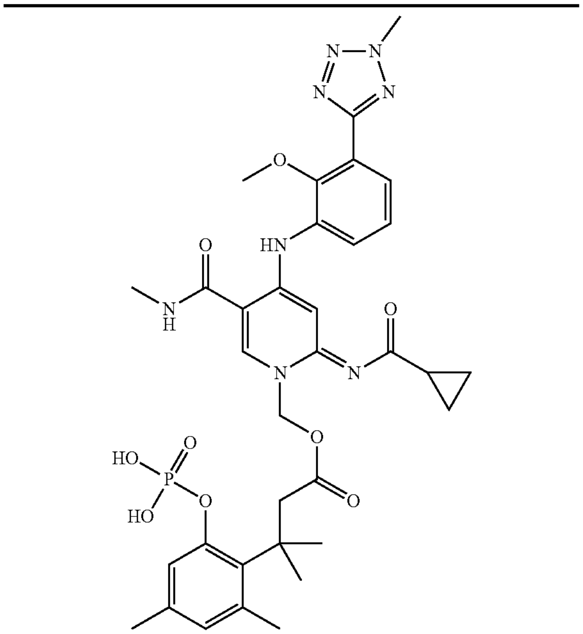
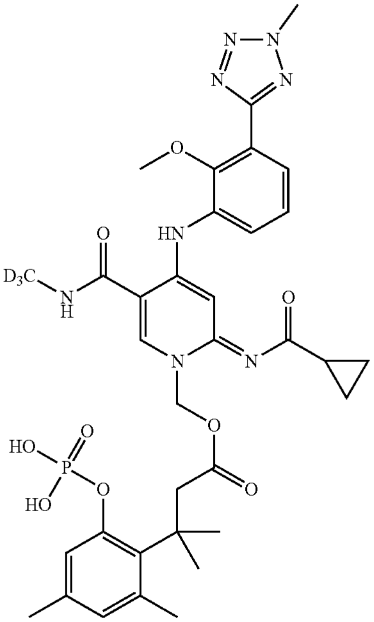 [SMILES: [2H]C([2H])([2H])NC(=O)c1cn(COC(=O)CC(C)(C)c2c(C)cc(C)cc2OP(=O)(O)O)/c(=N/C(=O)C2CC2)cc1Nc1cccc(-c2nnn(C)n2)c1OC]

-continued
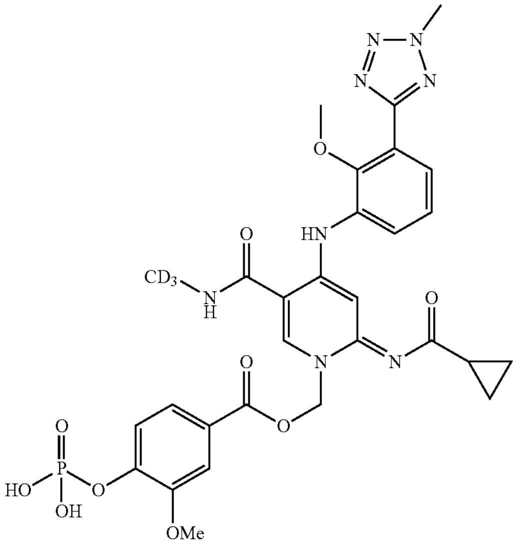 [SMILES: [2H]C([2H])([2H])NC(=O)c1cn(COC(=O)c2ccc(OP(=O)(O)O)c(OC)c2)/c(=N/C(=O)C2CC2)cc1Nc1cccc(-c2nnn(C)n2)c1OC]
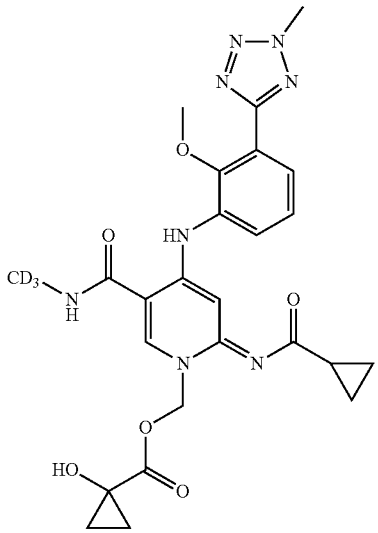 [SMILES: [2H]C([2H])([2H])NC(=O)c1cn(COC(=O)C2(O)CC2)/c(=N/C(=O)C2CC2)cc1Nc1cccc(-c2nnn(C)n2)c1OC]
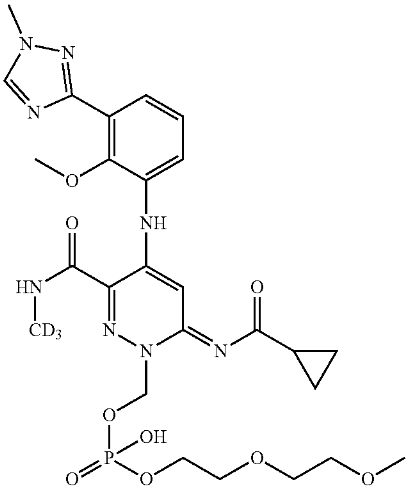 [SMILES: [2H]C([2H])([2H])NC(=O)c1nn(COP(=O)(O)OCCOCCOC)/c(=N/C(=O)C2CC2)cc1Nc1cccc(-c2ncn(C)n2)c1OC]
-continued
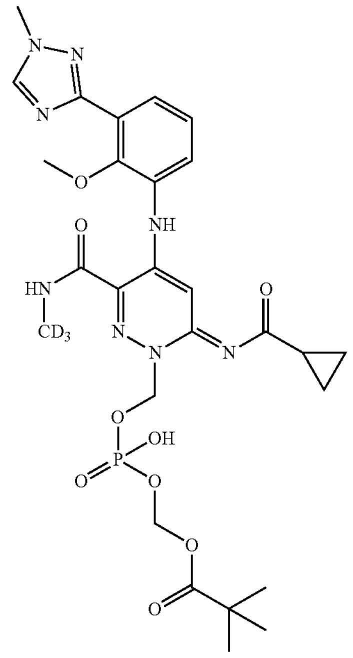 [SMILES: [2H]C([2H])([2H])NC(=O)c1nn(COP(=O)(O)OCOC(=O)C(C)(C)C)/c(=N/C(=O)C2CC2)cc1Nc1cccc(-c2ncn(C)n2)c1OC]
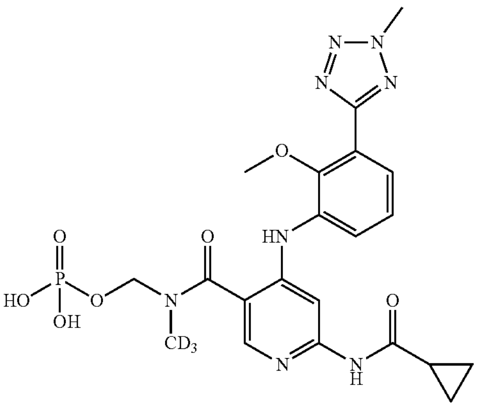 [SMILES: [2H]C([2H])([2H])N(COP(=O)(O)O)C(=O)c1cnc(NC(=O)C2CC2)cc1Nc1cccc(-c2nnn(C)n2)c1OC]

-continued
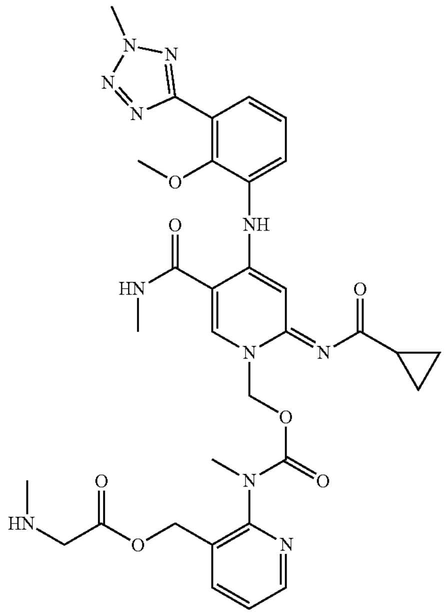 [SMILES: CNCC(=O)OCc1cccnc1N(C)C(=O)OCn1cc(C(=O)NC)c(Nc2cccc(-c3nnn(C)n3)c2OC)c/c1=N\C(=O)C1CC1]
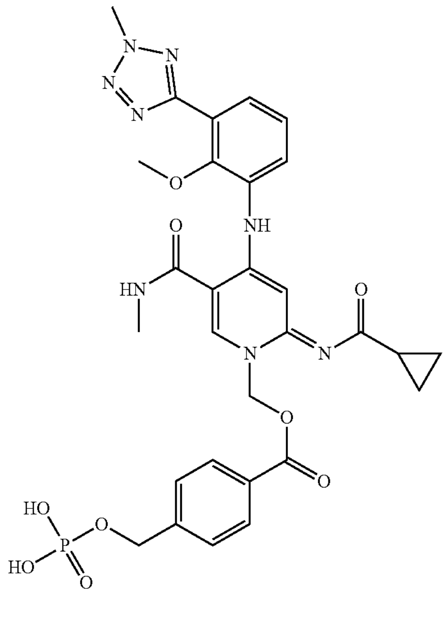 [SMILES: CNC(=O)c1cn(COC(=O)c2ccc(COP(=O)(O)O)cc2)/c(=N/C(=O)C2CC2)cc1Nc1cccc(-c2nnn(C)n2)c1OC]
-continued
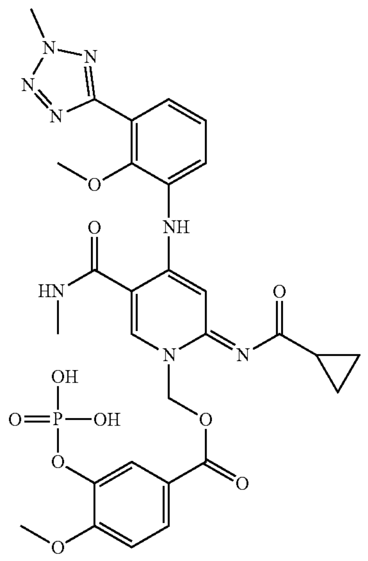 [SMILES: CNC(=O)c1cn(COC(=O)c2ccc(OC)c(OP(=O)(O)O)c2)/c(=N/C(=O)C2CC2)cc1Nc1cccc(-c2nnn(C)n2)c1OC]
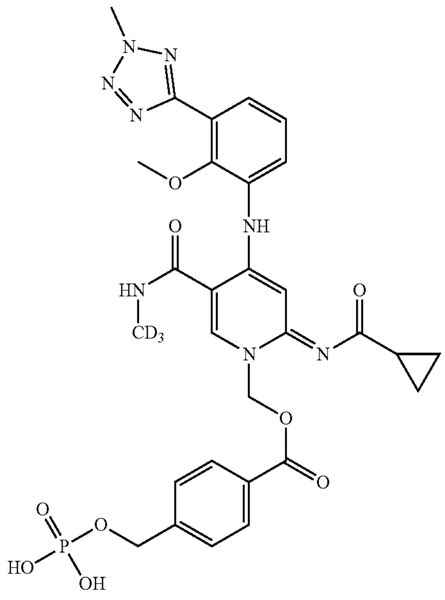 [SMILES: [2H]C([2H])([2H])NC(=O)c1cn(COC(=O)c2ccc(COP(=O)(O)O)cc2)/c(=N/C(=O)C2CC2)cc1Nc1cccc(-c2nnn(C)n2)c1OC]
or a salt thereof.

In a third aspect of the invention, there is provided a prodrug of compound (I) as shown below
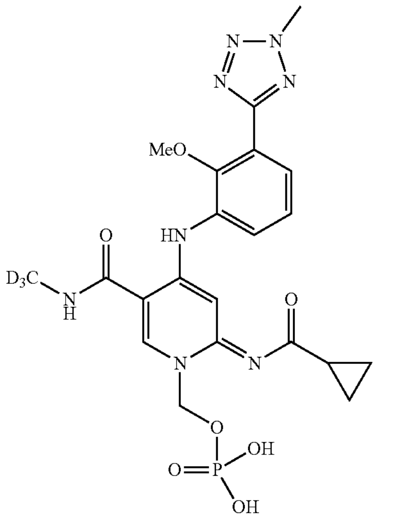 [SMILES: [2H]C([2H])([2H])NC(=O)c1cn(COP(=O)(O)O)/c(=N/C(=O)C2CC2)cc1Nc1cccc(-c2nnn(C)n2)c1OC]
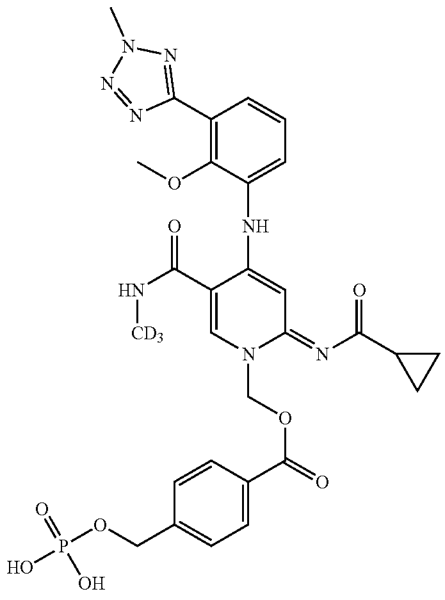 [SMILES: [2H]C([2H])([2H])NC(=O)c1cn(COC(=O)c2ccc(COP(=O)(O)O)cc2)/c(=N/C(=O)C2CC2)cc1Nc1cccc(-c2nnn(C)n2)c1OC]
-continued
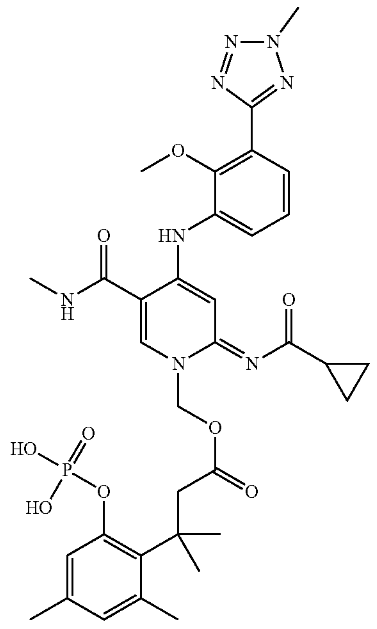 [SMILES: CNC(=O)c1cn(COC(=O)CC(C)(C)c2c(C)cc(C)cc2OP(=O)(O)O)/c(=N/C(=O)C2CC2)cc1Nc1cccc(-c2nnn(C)n2)c1OC]
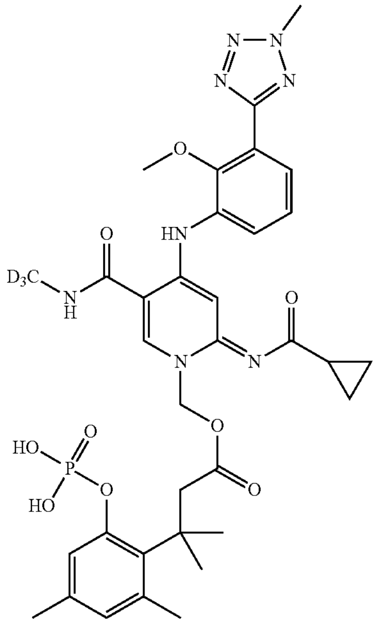 [SMILES: [2H]C([2H])([2H])NC(=O)c1cn(COC(=O)CC(C)(C)c2c(C)cc(C)cc2OP(=O)(O)O)/c(=N/C(=O)C2CC2)cc1Nc1cccc(-c2nnn(C)n2)c1OC]

-continued
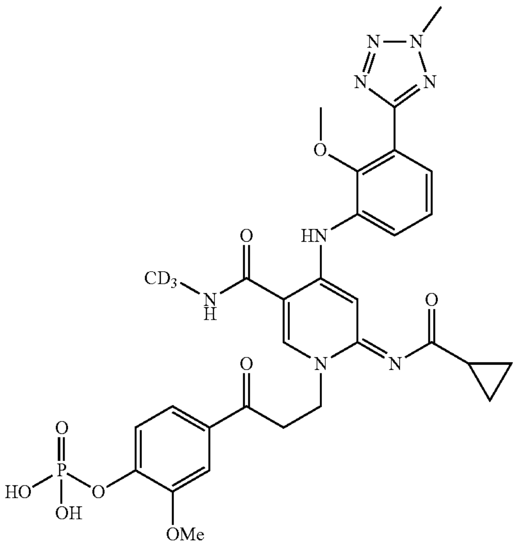
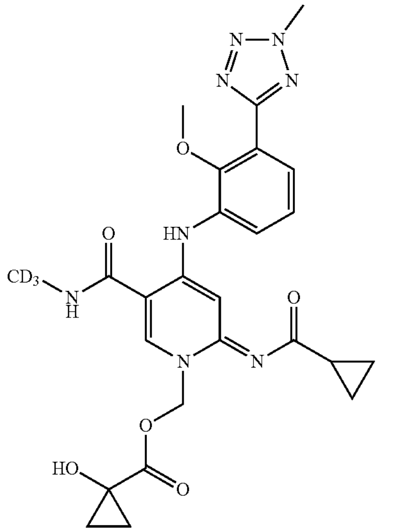 [SMILES: [2H]C([2H])([2H])NC(=O)c1cn(COC(=O)C2(O)CC2)/c(=N/C(=O)C2CC2)cc1Nc1cccc(-c2nnn(C)n2)c1OC]
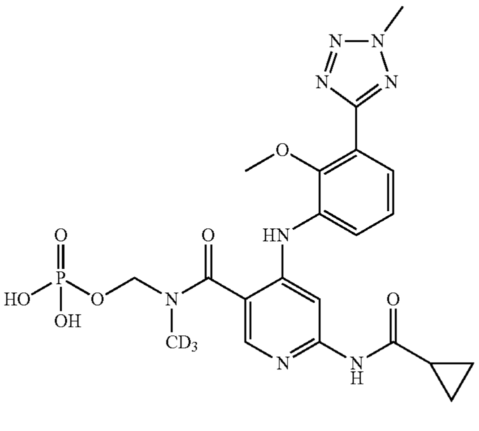 [SMILES: [2H]C([2H])([2H])N(COP(=O)(O)O)C(=O)c1cnc(NC(=O)C2CC2)cc1Nc1cccc(-c2nnn(C)n2)c1OC]
-continued
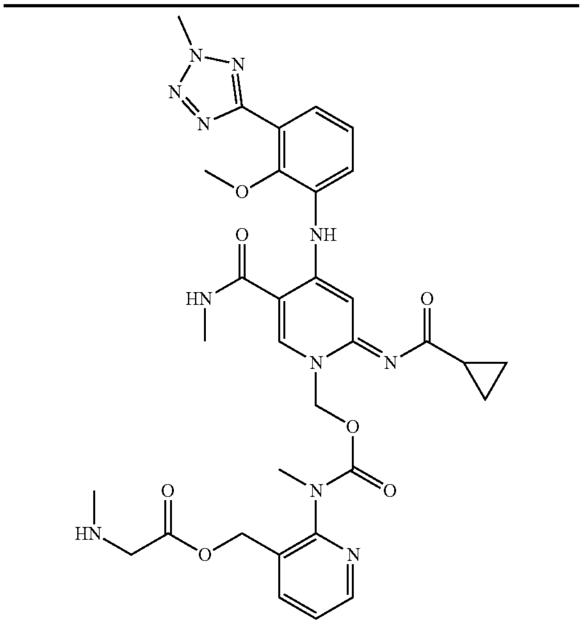
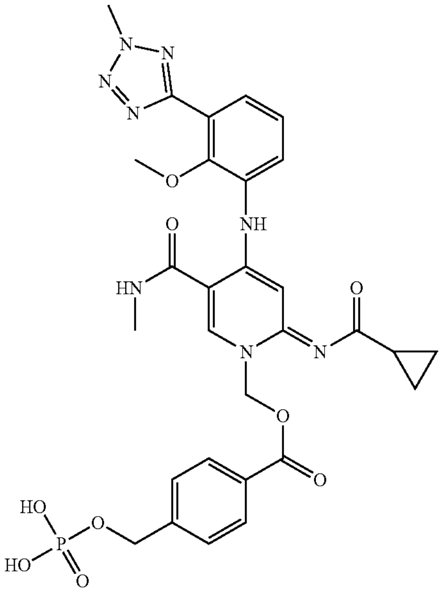 [SMILES: CNC(=O)c1cn(COC(=O)c2ccc(COP(=O)(O)O)cc2)/c(=N/C(=O)C2CC2)cc1Nc1cccc(-c2nnn(C)n2)c1OC]

-continued

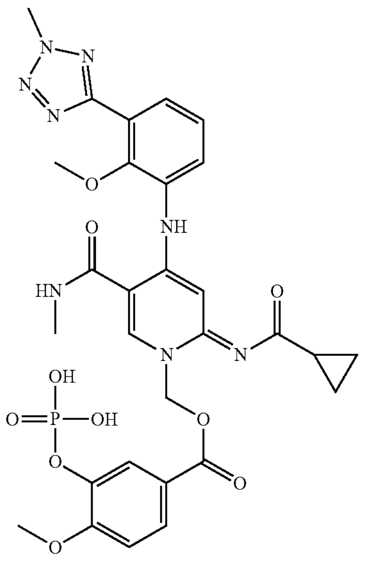 [SMILES: CNC(=O)c1cn(COC(=O)c2ccc(OC)c(OP(=O)(O)O)c2)/c(=N/C(=O)C2CC2)cc1Nc1cccc(-c2nnn(C)n2)c1OC]

or a salt thereof.

In a fourth aspect of the invention, there is provided a prodrug of compound (II) as shown below

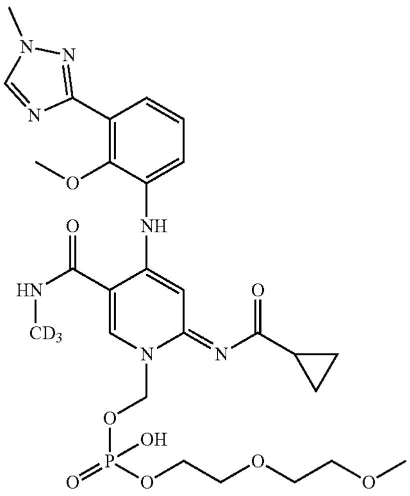

-continued

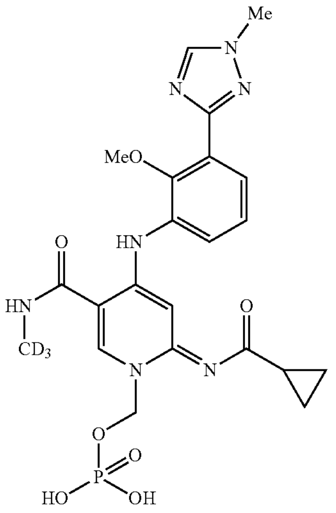 [SMILES: [2H]C([2H])([2H])NC(=O)c1cn(COP(=O)(O)O)/c(=N/C(=O)C2CC2)cc1Nc1cccc(-c2ncn(C)n2)c1OC]

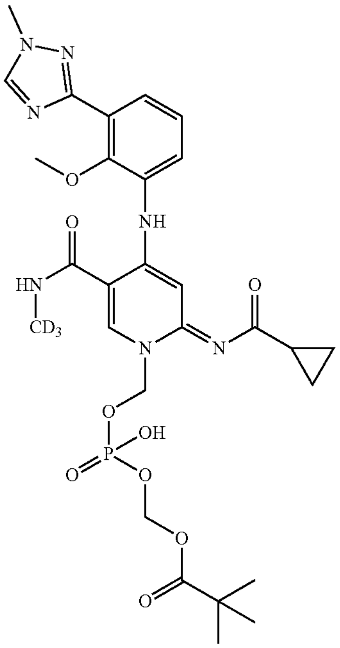 [SMILES: [2H]C([2H])([2H])NC(=O)c1cn(COP(=O)(O)OCOC(=O)C(C)(C)C)/c(=N/C(=O)C2CC2)cc1Nc1cccc(-c2ncn(C)n2)c1OC]

or a salt thereof.

In another aspect, there is provided a compound selected from the exemplified examples within the scope of the first aspect, or a pharmaceutically acceptable salt or stereoisomer thereof.

In another aspect, there is provided a compound selected from any subset list of compounds within the scope of any of the above aspects.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenia purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenia purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

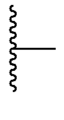

In accordance with a convention used in the art, is used in structural formulas herein to depict the bond that is the point of attachment of the moiety or substituent to the core or backbone structure.

A dash "-" that is not between two letters or symbols is used to indicate a point of attachment for a substituent. For example, $-CONH_2$ is attached through the carbon atom.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

All stereoisomers of the compounds, if applicable, of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting onTyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually;

bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Chemical names were determined using ChemDraw Ultra, version 9.0.5 (CambridgeSoft). The following abbreviations may be used:

| Abbreviations | |
|---|---|
| Ac | acetyl |
| AcOH | acetic acid |
| anhyd. | anhydrous |
| aq. | aqueous |

-continued

| Abbreviations | |
|---|---|
| Bn | benzyl |
| Bu | butyl |
| Boc | tert-butoxycarbonyl |
| BOP | benzotriazol-1-yloxytris-(dimethylamino)-phosphonium hexafluorophosphate |
| CV | Column Volumes |
| DCE | dichloroethane |
| DCM | dichloromethane |
| DDI | distilled de-ionized water |
| DIPEA | diisopropylethylamine |
| DMF | dimethylformamide |
| DMAP | 4-dimethylaminopyridine |
| DMSO | dimethylsulfoxide |
| ES/ESI | electrospray ionization |
| EtOAc | ethyl acetate |
| Et | ethyl |
| EtOH | ethanol |
| H or $H_2$ | hydrogen |
| h, hr or hrs | hour(s) |
| HATU | O-(7-azabenzotriazol-1-yl)-N,N,N',N'-tetramethyluronium hexafluorophosphate |
| hex | hexane |
| i | iso |
| IPA | isopropyl alcohol |
| ISCO | automated chromatography |
| HOAc/AcOH | acetic acid |
| HCl | hydrochloric acid |
| HPLC | high pressure liquid chromatography |
| LC | liquid chromatography |
| LiHMDS | Lithium bis(trimethylsilyl)amide |
| M | molar |
| mM | millimolar |
| Me | methyl |
| MeCN | acetonitrile |
| MeOH | methanol |
| MHz | megahertz |
| min. | minute(s) |
| mins | minute(s) |
| M + 1 | (M + H)+ |
| MS | mass spectrometry |
| n or N | normal |
| nm | nanometer |
| nM | nanomolar |
| NMP | N-methylpyrrolidine |
| $Pd_2dba_3$ | Tris(dibenzylideneacetone)dipalladium(0) |
| Ph | phenyl |
| $PPh_3$ | triphenylphosphine |
| Pr | propyl |
| PSI | pounds per square inch |
| rb | round bottle |
| Rt/RT | room temperature |
| Ret Time | retention time |
| sat. | saturated |
| SFC | supercritical fluid chromatography |
| TEA | triethylamine |
| TFA | trifluoroacetic acid |
| THF | tetrahydrofuran |
| xantphos | 4,5-bis(diphenylphosphino)-9,9-dimethylxanthene |

Analytical Purity of the Compounds was Determined by Using the Following Methods:

Analytical HPLC method A: SUNFIRE C18 [150×4.6 mm] column; 0.05% trifluoroacetic acid in water with pH 2.5 as buffer; mobile phase A=buffer:MeCN [95:5]; mobile phase B:MeCN:buffer [95:5]; 10% B to 100% B; 23 min; Flow rate: 1.0 mL/min);

Analytical HPLC method B: XBridge Phenyl C18 [150×4.6 mm] column; 0.05% trifluoroacetic acid in water pH 2.5 as buffer; mobile phase A-buffer:MeCN [95:5]; mobile phase B:MeCN:buffer [95:5]; 10% B to 100% B; 23 min; Flow rate: 1.0 mL/min);

Analytical LCMS method C:BEH C18 [2.1×50 mm, 1.7 μm particles] column; 0.05% trifluoroacetic acid as buffer; mobile phase A-water; mobile phase B: MeCN; 2% B to 98% B (0 to 1 min); 98% B (1 min to 1.5 min); 98%-2% B (1.5 min to 1.6 min). Gradient time (total)=1.6 min. Analysis time=2.2 min. Flow rate: 0.8 mL/min. Detectors: UV at 254 nM and MS (ESI+)

Example 1

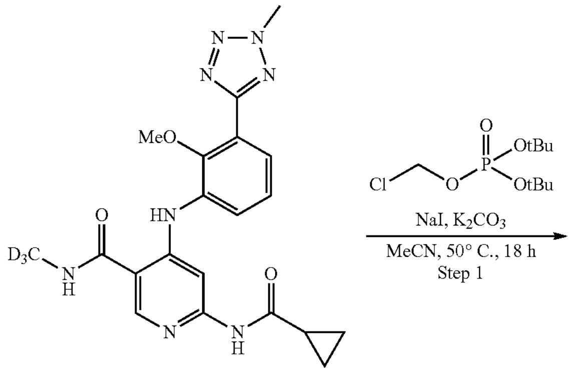

6-(cyclopropanecarboxamido)-4-((2-methoxy-3-(2-methyl-2H-tetrazol-5-yl)phenyl)amino)-N-methylnicotinamide

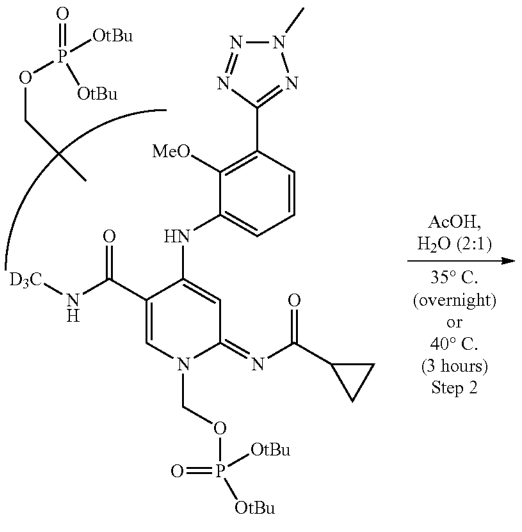

+ various other alkylated forms (minor)

-continued

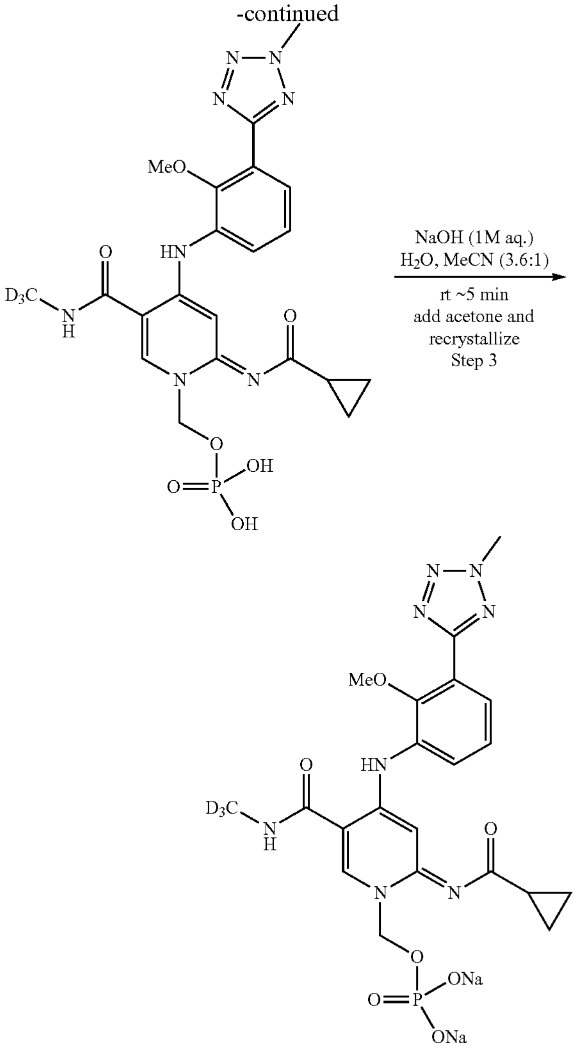

Step 1:

6-(cyclopropanecarboxamido)-4-((2-methoxy-3-(2-methyl-2H-tetrazol-5-yl)phenyl)amino)-N-methylnicotinamide (11 g, 25.9 mmol) and potassium carbonate (10.72 g, 78 mmol) were combined in a 500 mL flask with 260 mL of acetonitrile (commercial grade anhydrous). The slurry was stirred for 30 minutes at room temperature and then sodium iodide (11.63 g, 78 mmol) and di-tert-butyl (chloromethyl) phosphate (27.3 wt % in MeCN, density=0.824 g/mL, 89 mL, 78 mmol) were added. The vessel was equipped with a water cooled condenser and heated to 50° C. for 18 hours. The reaction is cooled to room temperature and filtered through celite, eluting with ~800 mL of DCM:MeOH (1:1). The filtrate was concentrated and carried on. Bis-alkylated (major): LC retention time 0.92 [C]. MS (E+) m/z: 870.7 ($MH^+$). Mono-alkylated (regioisomer unknown): LC retention time 0.82 [C]. MS (E+) m/z: 648.5 ($MH^+$).

Step 2:

The crude product of Step 1 was dissolved in acetic acid (28.8 mL) and water (14 mL), the solution was initially homogenous but became a slurry as the product was formed. Once the conversion to the desired material was complete water (~200 mL) was added. The slurry is sonicated and then stirred at room temperature. The vessel was cooled briefly in the freezer until the solution was below room temperature, at which point the precipitate was filtered off and rinsed with water (15 mL). The filter cake was air dried and then washed with diethyl ether (1 L). The solid was collected, sonicated in DCM (20 mL) and then filtered, collecting the resulting solid (4.6 g). LC retention time 0.59 [C]. MS (E+) m/z: 536.1 ($MH^+$).

Step 3:

The free acid (6.75 g, ~90% pure by HPLC) was suspended in MeCN (25 mL) and DDI water (90 mL). To this was added 1 M NaOH (aq., 27.7 mL, 27.7 mmol) over ~1 min. The thick brown suspension became a fine milky suspension. After 5 minutes of stirring the solution was filtered through two medium grade glass frits, providing a slightly cloudy yellow solution. Water (200 mL) was added to generate a nearly homogenous solution. To this was added acetone until the total volume was ~3 L at this point seed crystals were added and immediately fine white crystals formed, that rapidly increased in quantity. After 15 minutes a fine suspension prevailed. After 30 additional minutes additional acetone was added (total volume=4 L) and the suspension was stored at 8° C. overnight. The solid was collected by filtration, rinsing with acetone. The solid was collected and then triturated and sonicated in ~200 mL of acetone. The product was collected by filtration and dried overnight under vacuum (<0.1 torr) to provide 4.75 g of small yellow crystals (72% yield, 8.12 mmol). $^{13}C$ NMR (126 MHz, DEUTERIUM OXIDE) δ 182.7, 167.6, 161.7, 156.4, 153.4, 150.4, 140.5, 133.5, 126.3, 125.8, 125.3, 120.8, 109.3, 99.4, 74.4, 74.4, 61.2, 39.6, 17.2, 7.7. $^1H$ NMR (500 MHz, DEUTERIUM OXIDE) δ 8.43 (s, 1H), 7.58 (dd, J=1.22, 7.78 Hz, 1H), 7.43 (dd, J=1.22, 7.93 Hz, 1H), 7.25 (t, J=7.93 Hz, 1H), 6.95 (s, 1H), 5.60 (d, J=9.16 Hz, 2H), 4.38 (s, 3H), 3.56 (s, 3H), 1.60-1.72 (m, 1H), 0.66-0.81 (m, 4H)

LC retention time 0.59 [C]. MS (E+) m/z: 536.1 ($MH^+$).

Example 2

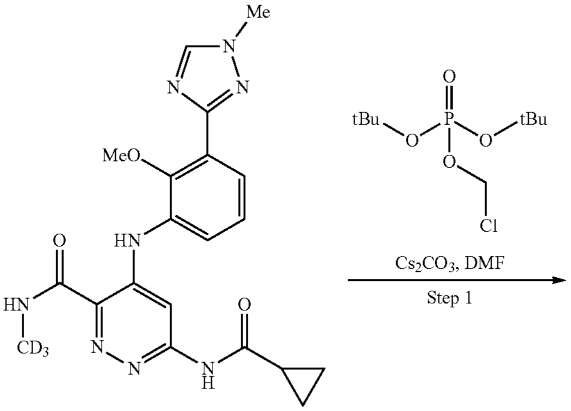

6-(cyclopropanecarboxamido)-4-((2-methoxy-3-(1-methyl-1H-1,2,4-triazol-3-yl)phenyl)amino)-N-(methyl-d3)pyridazine-3-carboxamide -continued

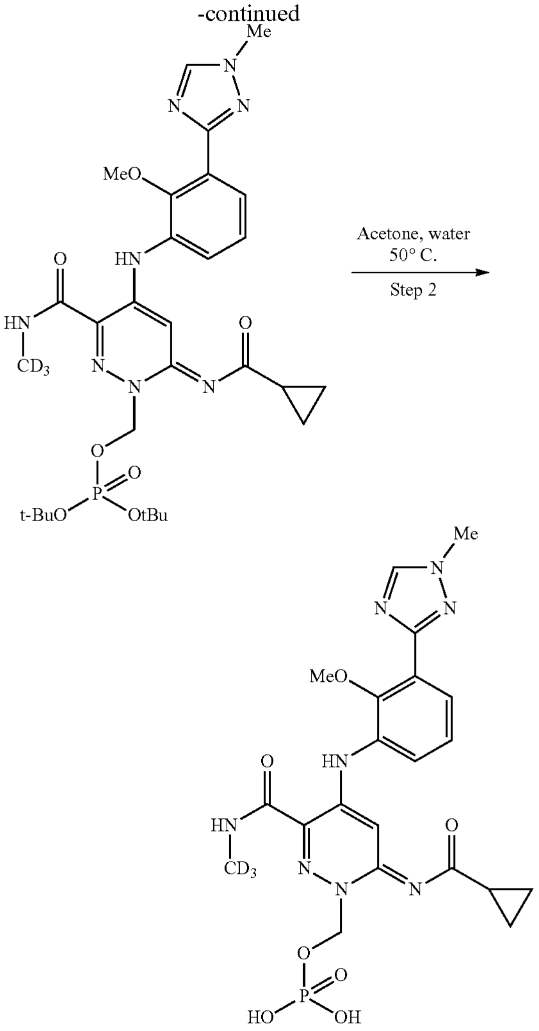

Step 1

To a suspension of 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide (0.5 g, 1.175 mmol) in DMF (9.04 mL) was added cesium carbonate (11.49 g, 35.3 mmol) as a single lot and the resultant mixture was stirred for 30 minutes at room temperature. Then di-tert-butyl (chloromethyl)phosphate (1.288 mL, 5.88 mmol) was added to the reaction and the reaction mixture was stirred at room temperature for 15 hours. After 15 hours the reaction was incomplete so additional di-tert-butyl (chloromethyl)phosphate (1.288 ml, 5.88 mmol) was added and the reaction continued for another 24 hours. Water was added to the reaction mixture and the product extracted with ethyl acetate (×2), the combined organic layers were washed with water and brine and then dried over anhydrous sodium sulfate, filtered and concentrated. The crude product was carried on as recovered. LC retention time 0.77 [C]. MS (E+) m/z: 648.5 ($MH^+$).

Step 2

The crude mixture from Step 1 was dissolved in acetone (4 mL) and water (4 mL) and the solution was heated to 50° C. until the reaction was complete (1 hour). The reaction was concentrated under reduced pressure using a rotary evaporator and a room temperature heating bath. The crude product was diluted with water (total volume=60 mL) and then washed with DCM (~500 mL×2). The aqueous layer was loaded directly onto a reverse phase (gold) isco 50 g cartridge and purified using a water (DDI, no buffer)/MeCN (no buffer) gradient (0-40% MeCN: $H_2O$). $^1H$ NMR (400 MHz, DMSO-$d_6$) δ 11.74 (s, 1H), 9.38 (br. s., 1H), 8.58 (s, 1H), 8.21 (s, 1H), 7.83 (d, J=7.9 Hz, 1H), 7.56 (d, J=6.7 Hz, 1H), 7.36 (t, J=7.9 Hz, 1H), 5.91 (d, J=11.7 Hz, 2H), 3.95 (s, 3H), 3.76 (s, 3H), 2.32 (d, J=1.8 Hz, 1H), 1.06-0.76 (m, 4H). LC retention time 0.54 [C]. MS (E+) m/z: 536.4 ($MH^+$). Structure determined in part by analogy to Example 1, also by the small molecule crystal structure of a decomposition product that resulted from extended exposure to sodium hydroxide:

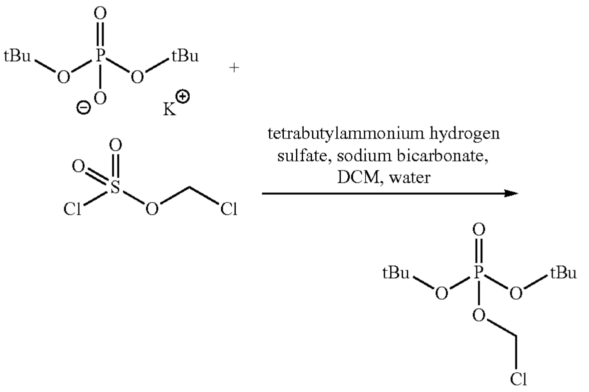

A solution of potassium di-tert-butyl phosphate (8.5 g, 34.2 mmol), sodium bicarbonate (11.50 g, 137 mmol) and tetrabutylammonium hydrogensulfate (1.162 g, 3.42 mmol) in DCM (104 mL) and water (124 mL) was prepared and stirred at 0° C. for 15 minutes. To this was added chloromethyl sulfochloridate (6.93 mL, 68.5 mmol) and the reaction mixture was brought to room temperature stirred overnight. The reaction mixture was diluted with DCM (100 ml) and washed with water (4×200 mL) and then with brine. The organic layer was dried over anhydrous sodium sulfate, filtered and concentrated in vacuo without heating (temperature maintained below 25° C.) to get colorless liquid.

$^1H$ NMR (500 MHz, CHLOROFORM-d) δ 5.58 (d, J=14.8 Hz, 2H), 1.46 (d, J=0.8 Hz, 18H)

Example 3

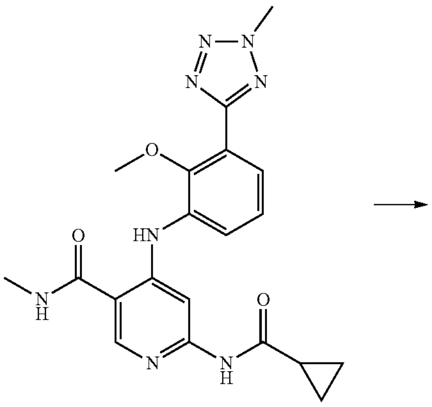

-continued

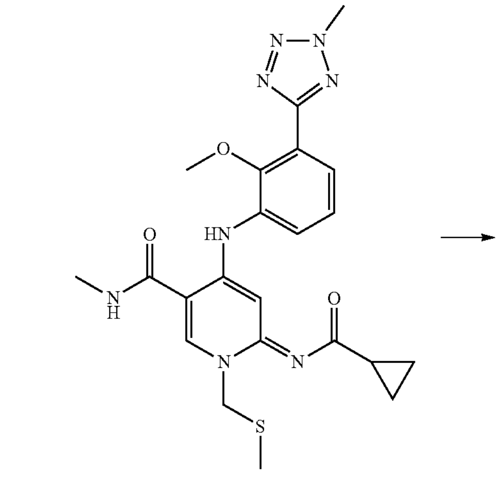

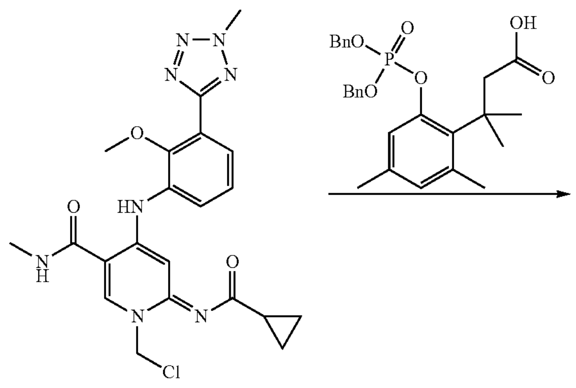

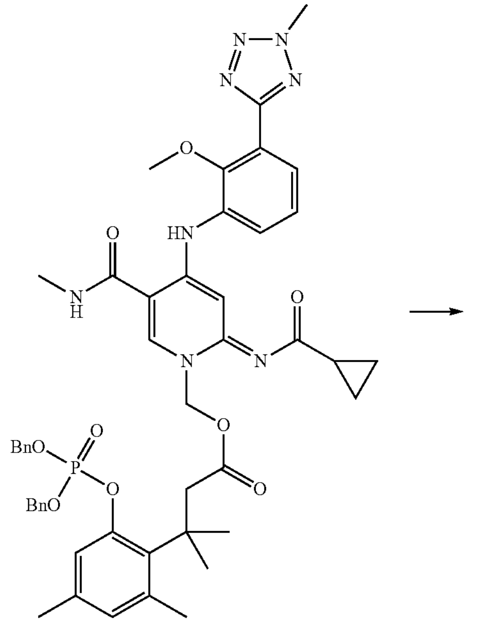

-continued

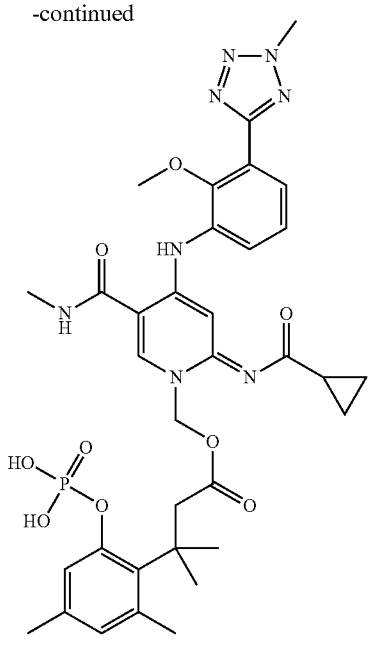

Step 1

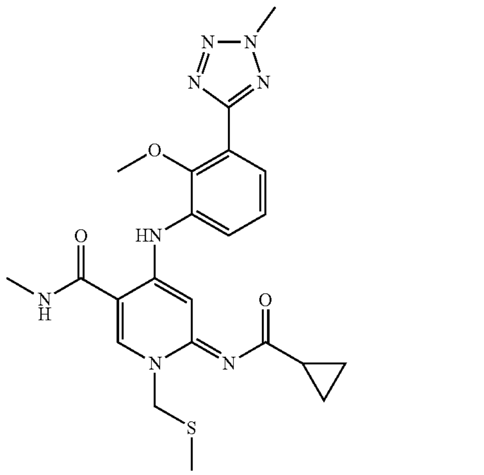

(E)-6-((Cyclopropanecarbonyl)imino)-4-((2-methoxy-3-(2-methyl-2H-tetrazol-5-yl)phenyl)amino)-N-methyl-1-((methylthio)methyl)-1,6-dihydropyridine-3-carboxamide To a solution of 6-(cyclopropanecarboxamido)-4-((2-methoxy-3-(2-methyl-2H-tetrazol-5-yl)phenyl)amino)-N-methylnicotinamide (0.500 g, 1.184 mmol) in DMF (10 mL), was added potassium carbonate (0.981 g, 7.10 mmol). The mixture was stirred at RT for 30 min and then chloromethyl methyl sulfide (0.977 mL, 11.84 mmol) and sodium iodide (0.887 g, 5.92 mmol) were added. The mixture was stirred at 50° C. for 16 h under nitrogen. The reaction mixture was diluted with water and extracted with ethyl acetate (3×50 mL). The organic layer was dried over anhydrous sodium sulphate and concentrated in vacuum. The residue was purified by RP-HPLC (Preparative column: kinetex C18 (150×21.2 mm; 5 micron), mobile phase A: 10 mM ammonium acetate with 4.5 pH, mobile phase B: acetonitrile, flow rate: 18 mL/min, gradient: 0/20, 30/100) gave the title compound (0.230 g, 0.477 mmol, 40.3% yield)

as a light yellow solid. $^1H$ NMR (400 MHz, DMSO-$d_6$) δ 0.64-0.76 (m, 4H), 1.45-1.56 (m, 1H), 2.26 (s, 3H), 2.82 (d, J=4.02 Hz, 3H), 3.74 (s, 3H), 4.46 (s, 3H), 5.21 (s, 2H), 7.36 (br. s, 1H), 7.66 (br. s, 2H), 8.00 (br. s, 1H), 8.50 (s, 1H), 8.55-8.69 (br. s, 1H); LC-MS (ES): m/z=483.2 $[M+H]^+$ Step 2

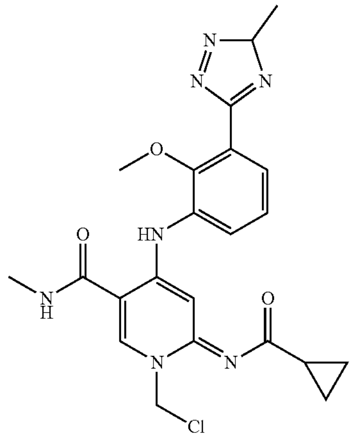

(E)-1-(Chloromethyl)-6-((cyclopropanecarbonyl)imino)-4-((2-methoxy-3-(2-methyl-2H-tetrazol-5-yl)phenyl)amino)-N-methyl-1,6-dihydropyridine-3-carboxamide To a solution of (E)-6-((cyclopropanecarbonyl)imino)-4-((2-methoxy-3-(2-methyl-2H-tetrazol-5-yl)phenyl)amino)-N-methyl-1-((methylthio)methyl)-1,6-dihydropyridine-3-carboxamide (0.100 g, 0.207 mmol) in dichloromethane (2.5 mL) at 0° C., sulfuryl chloride (0.084 mL, 1.036 mmol) was added. The mixture was stirred at 0° C. for 30 min and concentrated in vacuum at 30° C. to give the title compound (0.110 g, 0.198 mmol, 95% yield) as an off-white solid. The crude product was used as such. LC-MS (ES): m/z=471.2 $[M+H]^+$ Step 3

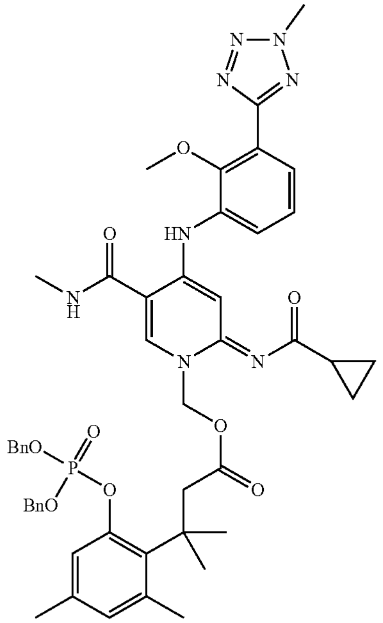

(E)-(2-((Cyclopropanecarbonyl)imino)-4-((2-methoxy-3-(2-methyl-2H-tetrazol-5-yl)phenyl)amino)-5-(methylcarbamoyl)pyridin-1(2H)-yl) methyl 3-(2-((bis(benzyloxy)phosphoryl)oxy)-4,6-dimethylphenyl)-3-methylbutanoate To a solution of (E)-1-(chloromethyl)-6-((cyclopropanecarbonyl)imino)-4-((2-methoxy-3-(2-methyl-2H-tetrazol-5-yl)phenyl)amino)-N-methyl-1,6-dihydropyridine-3-carboxamide (0.110 g, 0.234 mmol) and DIPEA (0.245 mL, 1.402 mmol) in tetrahydrofuran (2 mL) at 0° C., 3-(2-((bis(benzyloxy)phosphoryl)oxy)-4,6-dimethylphenyl)-3-methylbutanoic acid (0.169 g, 0.350 mmol) was added. The mixture was stirred at RT for 3 h and then was concentrated in vacuum at 30° C. to give the crude product as a brown gum. RP-HPLC purification (Preparative column: X-bridge phenyl (250×19 mm; 5 micron), mobile phase A: 10 mM ammonium acetate in water with 4.5 pH, mobile phase B: acetonitrile, flow rate: 18 mL/min, gradient: 0/30, 15/80) gave the title compound (0.115 g, 0.119 mmol, 50.8% yield) as an off-white solid. $^1H$ NMR (300 MHz, DMSO-$d_6$) δ 0.55-0.69 (m, 4H), 1.49 (s, 7H), 2.01-2.08 (s, 3H), 2.39 (s, 3H), 2.77 (d, J=4.15 Hz, 3H), 2.91 (s, 2H), 3.72 (s, 3H), 4.46 (s, 3H), 5.11 (d, J=8.31 Hz, 4H), 5.88 (br. s, 2H), 6.64 (s, 1H), 6.88 (s, 1H), 7.23-7.40 (m, 10H), 7.51-7.60 (m, 1H), 7.66 (br. s, 1H), 7.90 (br. s, 1H), 8.30 (s, 1H), 8.49-8.58 (m, 1H), 10.79 (s, 1H);

LC-MS (ES): m/z=917.4 $[M+H]^+$

Step 4

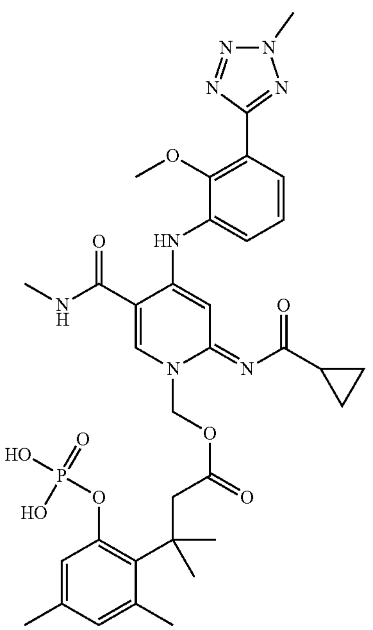

(E)-(2-((Cyclopropanecarbonyl)imino)-4-((2-methoxy-3-(2-methyl-2H-tetrazol-5-yl)phenyl)amino)-5-(methylcarbamoyl)pyridin-1(2H)-yl)methyl 3-(2,4-dimethyl-6-(phosphonooxy)phenyl)-3-methylbutanoate To a solution of (E)-(2-((cyclopropanecarbonyl)imino)-4-((2-methoxy-3-(2-methyl-2H-tetrazol-5-yl)phenyl)amino)-5-(methylcarbamoyl)pyridin-1(2H)-yl)methyl 3-(2-((bis(benzyloxy)phosphoryl)oxy)-4,6-dimethylphenyl)-3-methylbutanoate (0.090 g, 0.098 mmol) in 1,2-dichloroethane (4 mL) at 0° C., were added TFA (0.756 mL, 9.82 mmol) and anisole (0.536 mL, 4.91 mmol). After being stirred at 50° C. for 1 h, the solvent was removed under vacuum to give the crude product. After RP HPLC purification (Preparative column: Sunfire C18 (150×19 mm; 5 micron), mobile phase A: 10 mM ammonium acetate in water, mobile phase B: acetonitrile, flow rate: 18 mL/min, gradient: 0/10, 25/100), the title compound (0.015 g, 0.020 mmol, 20.52% yield) was obtained as an off-white solid. $^{1}H$ NMR (400 MHz, DMSO-$d_6$) δ 0.73-0.97 (m, 4H), 1.31-1.67 (m, 6H), 1.83-1.95 (m, 3H), 2.09-2.29 (m, 4H), 2.73-3.00 (m, 3H), 3.09-3.21 (m, 2H), 3.72-3.83 (m, 3H), 4.35-4.54 (m, 3H), 5.79-5.96 (m, 2H), 6.17-6.27 (m, 1H), 6.97-7.06 (m, 1H), 7.43-7.52 (m, 2H), 7.59-7.70 (m, 1H), 7.81-7.92 (m, 1H), 8.71-8.79 (m, 1H). LC-MS (ES): m/z=737.2 $[M+H]^+$; HPLC RT and purity: 6.410 min and 98.91% (method A) δ 7.749 min and 98.89% (method B).

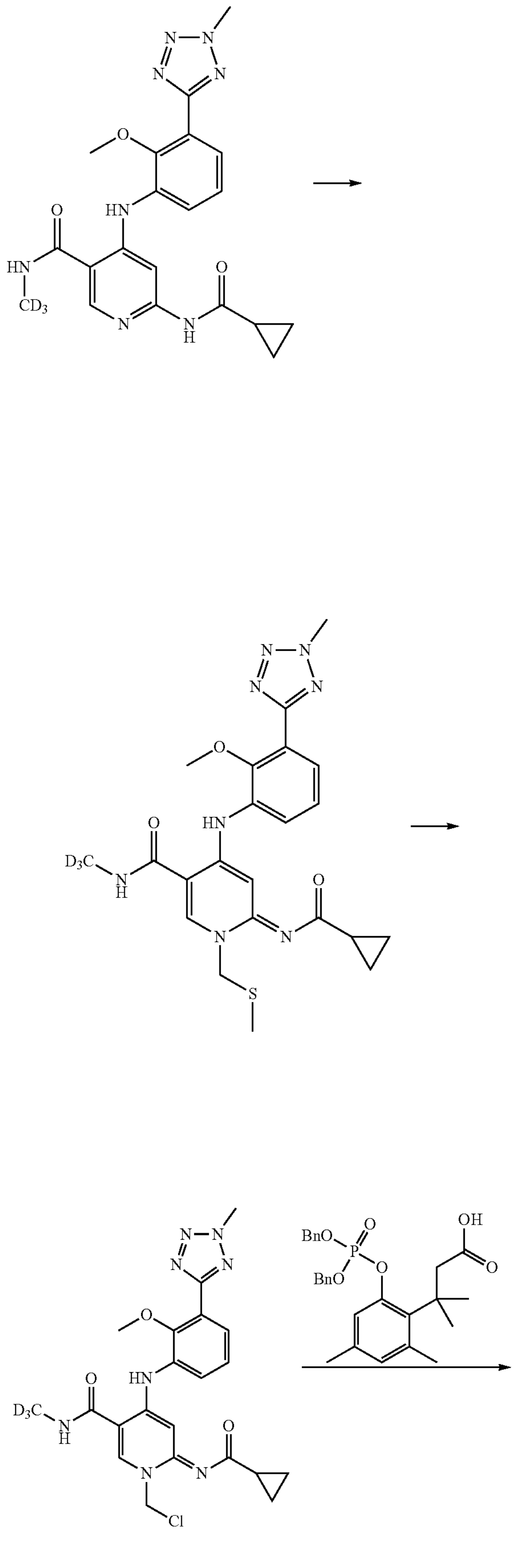

-continued

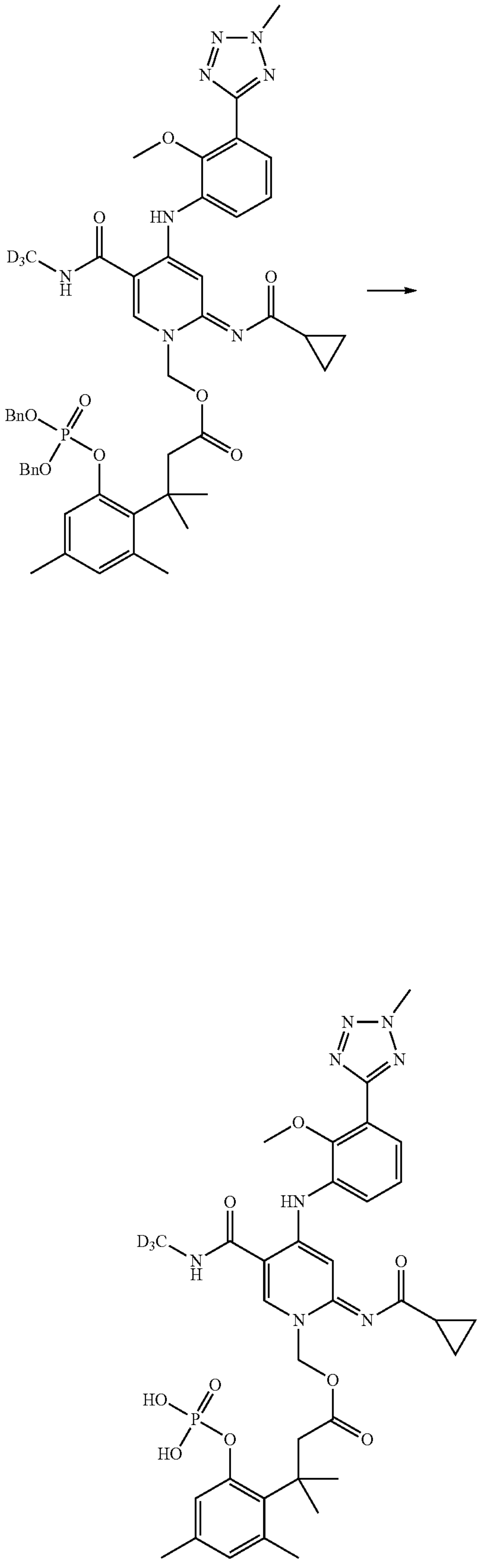

Step-1

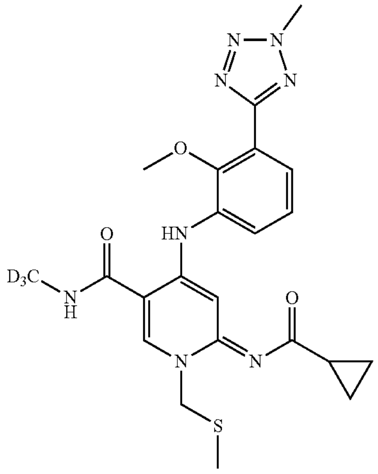 [SMILES: [2H]C([2H])([2H])NC(=O)c1cn(CSC)/c(=N/C(=O)C2CC2)cc1Nc1cccc(-c2nnn(C)n2)c1OC]

To a mixture of 6-(cyclopropanecarboxamido)-4-((2-methoxy-3-(2-methyl-2H-tetrazol-5-yl)phenyl)amino)-N-(methyl-$d_3$) nicotinamide (0.500 g, 1.175 mmol) and potassium carbonate (0.975 g, 7.05 mmol) in DMF (10 mL), chloromethyl methyl sulfide (0.970 mL, 11.75 mmol) and sodium iodide (0.881 g, 5.88 mmol) were added. After being stirred at 50° C. for 16 h under nitrogen, the reaction mixture was diluted with water and extracted with ethyl acetate (3×50 mL). The organic layer was dried over anhydrous sodium sulphate and concentrated in vacuum to give the crude product. RP-HPLC purification of the crude product (Preparative column: Sunfire C18 (150×4.6 mm; 5 micron), mobile phase A: 10 mM ammonium acetate, mobile phase B: acetonitrile, flow rate: 1.0 mL/minute, gradient: 0/10, 20/100) gave the title compound (0.210 g, 0.424 mmol, 36.1% yield) as a light yellow solid. $^1$H NMR (300 MHz, DMSO-$d_6$) δ 0.58-0.79 (m, 4H), 1.52-1.58 (m, 1H), 2.07 (s, 3H), 3.74 (s, 3H), 4.46 (s, 3H), 5.21 (s, 2H), 7.35 (t, J=7.80 Hz, 1H), 7.60 (br. S, 1H), 7.66 (d, J=7.93 Hz, 1H), 7.90-8.04 (br. S, 1H), 8.49 (s, 1H), 8.56-8.65 (br. S, 1H), 10.71 (br. S, 1H); LC-MS (ES): m/z=486.2 $[M+H]^+$ Step 2

€-1-(Chloromethyl)-6-((cyclopropanecarbonyl)imino)-4-((2-methoxy-3-(2-methyl-2H-tetrazol-5-yl)phenyl)amino)-N-(methyl-$d_3$)-1,6-dihydropyridine-3-carboxamide

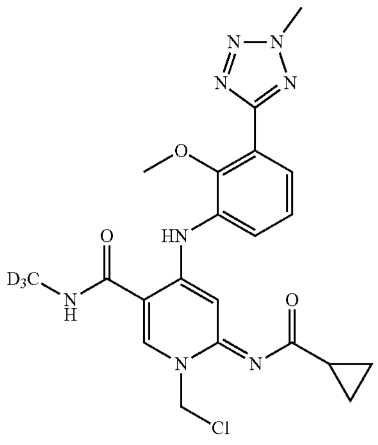 [SMILES: [2H]C([2H])([2H])NC(=O)c1cn(CCl)/c(=N/C(=O)C2CC2)cc1Nc1cccc(-c2nnn(C)n2)c1OC]

To a solution of €-6-((cyclopropanecarbonyl)imino)-4-((2-methoxy-3-(2-methyl-2H-tetrazol-5-yl)phenyl)amino)-N-methyl-1-((methylthio)methyl)-1,6-dihydropyridine-3-carboxamide (0.100 g, 0.206 mmol) in dichloromethane (2.5 mL) at 0° C., sulfuryl dichloride (0.083 mL, 1.030 mmol) was added. The mixture was stirred at 0° C. for 30 min. The reaction mixture was concentrated in vacuum at 30° C. to give the title compound (0.112 g, 0.199 mmol, 96% yield) as an off-white solid. The crude product was used as such in the next step. LC-MS (ES): m/z=474.2 $[M+H]^+$ Step 3

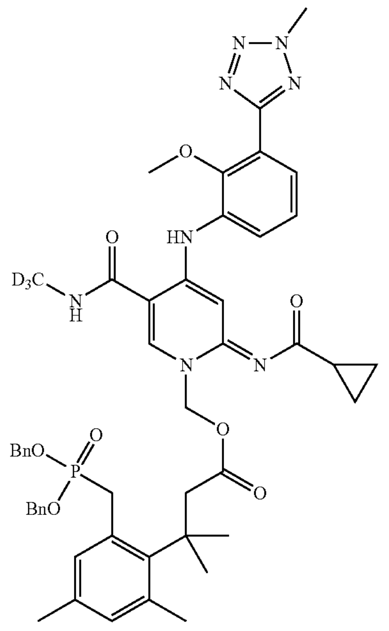

∈-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1(2H)-yl) methyl 3-(2-((bis(benzyloxy)phosphoryl)oxy)-4,6-dimethylphenyl)-3-methylbutanoate To a solution of €-1-(chloromethyl)-6-((cyclopropanecarbonyl)imino)-4-((2-methoxy-3-(2-methyl-2H-tetrazol-5-yl)phenyl)amino)-N-methyl-1,6-dihydropyridine-3-carboxamide (0.112 g, 0.199 mmol), and DIPEA (0.208 mL, 1.191 mmol) in tetrahydrofuran (2 mL) at 0° C., 3-(2-((bis(benzyloxy)phosphoryl)oxy)-4,6-dimethylphenyl)-3-methylbutanoic acid (0.144 g, 0.298 mmol) was added. After being stirred at RT for 3 h, the reaction mixture was concentrated in vacuum at 30° C. The residue was purified by RP-HPLC purification (Preparative column: kinetex C18 (150×4.6 mm; 5 micron), mobile phase A: 10 mM ammonium acetate, mobile phase B: acetonitrile, flow rate: 1.0 mL/min, gradient: 0/30, 20/100, 25/100, 28/30, 33/30) to give the title compound (0.060 g, 0.063 mmol, 31.5% yield) as an off-white solid. $^1$H NMR (300 MHz, DMSO-$d_6$) δ 0.55-0.69 (m, 4H), 1.49 (s, 7H), 2.05 (s, 3H), 2.39 (s, 3H), 2.91 (s, 2H), 3.73 (s, 3H), 4.46 (s, 3H), 5.09 (s, 2H), 5.12 (s, 2H), 5.89 (br. S, 2H), 6.64 (s, 1H), 6.87 (s, 1H), 7.23-7.41 (m, 10H), 7.57 (d, J=6.00 Hz, 1H), 7.68 (d, J=7.20 Hz, 1H), 7.91 (br. S, 1H), 8.30 (s, 1H), 8.50 (br. S, 1H), 10.79 (br. S, 1H); LC-MS (ES): m/z=920.4 $[M+H]^+$ Step 4

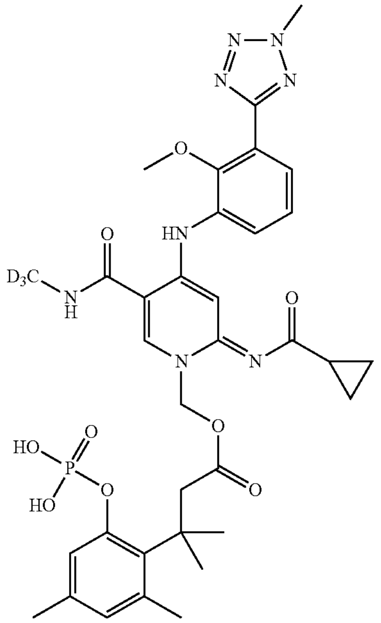

∈-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1(2H)-yl) methyl 3-(2,4-dimethyl-6-(phosphonooxy)phenyl)-3-methylbutanoate To a solution of €-(2-((cyclopropanecarbonyl)imino)-4-((2-methoxy-3-(2-methyl-2H-tetrazol-5-yl)phenyl)amino)-5-((methyl-$d_3$)carbamoyl)pyridin-1 (2H)-yl)methyl 3-(2-((bis(benzyloxy)phosphoryl)oxy)-4,6-dimethylphenyl)-3-methylbutanoate (0.045 g, 0.049 mmol) in 1,2-dichloroethane (2 mL) at 0° C., were added TFA (0.377 mL, 4.89 mmol) and anisole (0.267 mL, 2.446 mmol). The mixture was stirred at 50° C. for 1 h. The reaction mixture was concentrated under vacuum to give the crude product. RP-HPLC purification (Preparative column: Sunfire C18 (150×19 mm; 5 micron), mobile phase A: 0.1% HCOOH in water, mobile phase B: acetonitrile, flow rate: 18 mL/min, gradient: 0/30, 10/45) gave the title compound (0.014 g, 0.018 mmol, 37.5% yield) as an off-white solid. $^1$H NMR (400 MHz, DMSO-$d_6$) δ 0.79-0.88 (m, 4H), 1.50 (s, 6H), 1.95 (s, 3H), 2.12 (br. S, 1H), 2.32 (s, 3H), 3.16 (br. S, 2H), 3.78 (s, 3H), 4.48 (s, 3H), 5.90 (s, 2H), 6.30 (s, 1H), 7.05 (s, 1H), 7.48 (d, J=8.03 Hz, 2H), 7.66 (d, J=8.03 Hz, 1H), 7.86 (d, J=6.53 Hz, 1H), 8.80 (s, 1H), 10.10 (br. S, 1H), 11.67 (br. S, 1H); LC-MS (ES): m/z=740.4 $[M+H]^+$; HPLC RT and purity: 6.386 min and 97.03% (method A) δ 7.746 min and 97.45% (method B).

Example 5

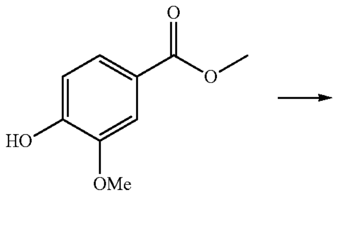

-continued

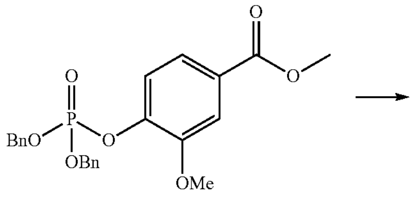

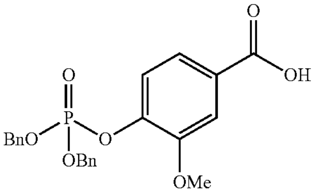

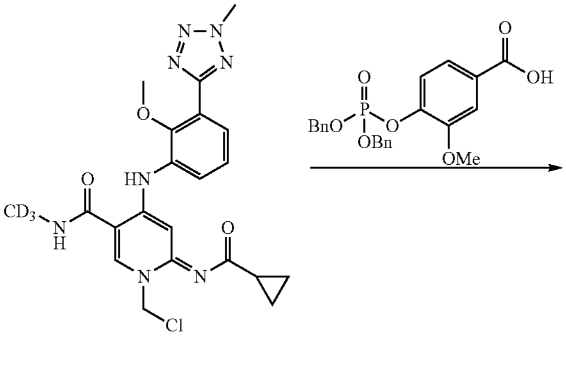

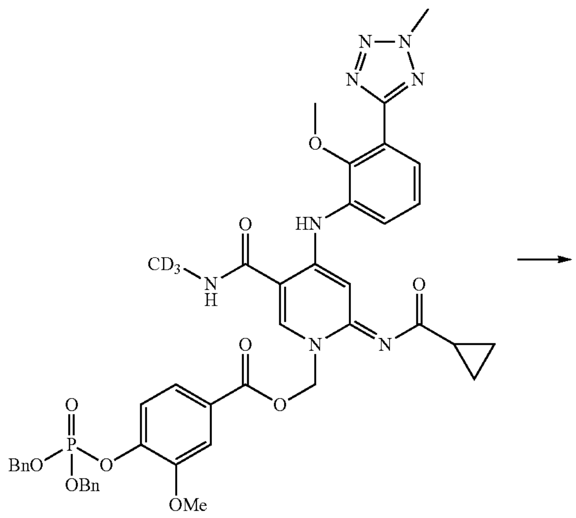

-continued

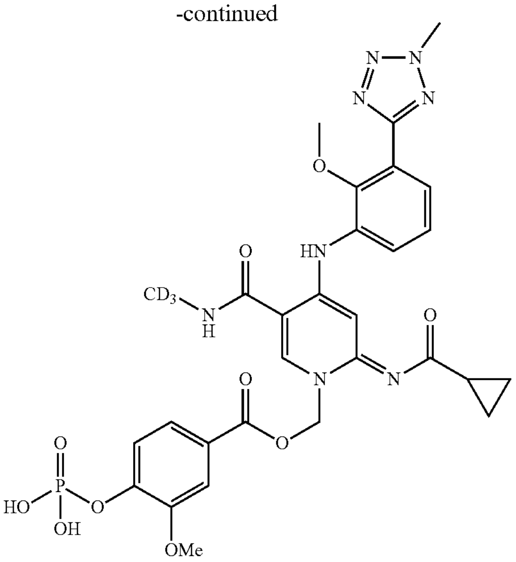

Step 1

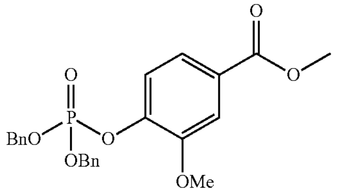

Methyl 4-((bis(benzyloxy)phosphoryl)oxy)-3-methoxybenzoate

To a solution of methyl 4-hydroxy-3-methoxybenzoate (3.000 g, 16.47 mmol) in dichloromethane (30 mL), was added dibenzyl-N,N-diisopropylphosphoramidite (8.30 mL, 24.70 mmol) followed by 1H-tetrazole (73.0 mL, 24.70 mmol) (0.45 M in acetonitrile) and the mixture was stirred at room temperature for 8 h. The reaction was cooled at 0° C. $H_2O_2$ (5.05 mL, 165 mmol) was added. After being stirred at room temperature for 2 h, the reaction mixture was concentrated to remove acetonitrile and the remaining aqueous layer was diluted with water, and extracted with ethyl acetate (3×100 mL). The combined organic layer was washed with brine, dried over anhydrous sodium sulfate, filtered and concentrated. The crude material was purified by ISCO [silica gel 60-120 mesh, column size 80 g, ethyl acetate in hexane as eluent]. The product was eluted at 30% ethyl acetate in hexane to get the title compound (8.200 g, 15.94 mmol, 97% yield) as a colourless oil. $^1H$ NMR (400 MHz, $CDCl_3$) δ 3.84 (s, 3H), 3.91 (s, 3H), 5.16 (s, 2H), 5.18 (s, 2H), 7.25 (d, J=8.00 Hz, 1H), 7.31-7.37 (m, 10H), 7.57 (d, J=9.20 Hz, 2H); LC-MS (ES): m/z=443.2 $[M+H]^+$ Step 2

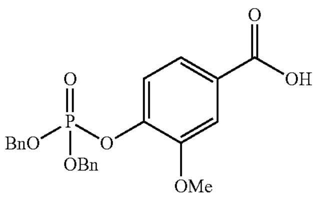

4-((bis(Benzyloxy)phosphoryl)oxy)-3-methoxybenzoic acid

To a solution of methyl 4-((bis(benzyloxy)phosphoryl)oxy)-3-methoxybenzoate (3.000 g, 5.83 mmol) in tetrahydrofuran (30 mL) and water (30 mL), was added LiOH (0.279 g, 11.66 mmol) at 0° C. After being stirred at 0° C. for 1 h, the mixture was extracted with ethyl acetate (2×100 mL). The aqueous layer was acidified with 1.5 N HCl solution (pH ~1) and extracted with ethyl acetate (3×100 mL). The organic layer was washed with brine solution, dried over anhydrous $Na_2SO_4$ and concentrated in vacuum to give the title compound (1.700 g, 1.746 mmol, 29.9% yield) as a colourless gum. The crude product was used as such. $^1$H NMR (400 MHz, DMSO-$d_6$) δ 3.80 (s, 3H), 5.17 (s, 2H), 5.20 (s, 2H), 6.85 (dd, J=2.40, 6.40 Hz, 1H), 7.40-7.52 (m, 10H), 7.53 (dd, J=2.00, 8.40 Hz, 1H), 7.59 (s, 1H), 12.60 (br. s, 1H). LC-MS (ES): m/z=429.0 [M+H]$^+$ Step 3

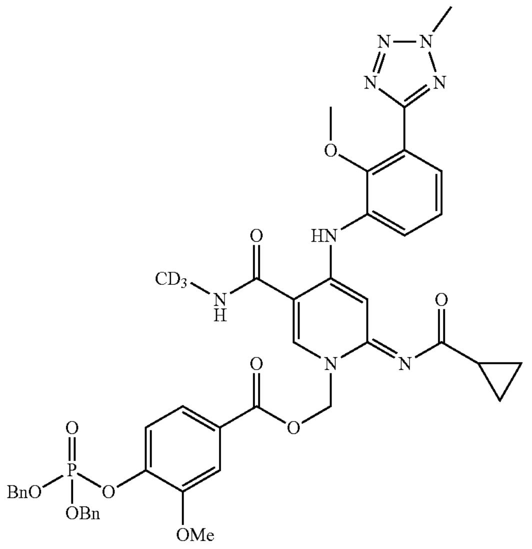

(E)-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1(2H)-yl) methyl 4-((bis(benzyloxy)phosphoryl)oxy)-3-methoxybenzoate To a solution of (E)-1-(chloromethyl)-6-((cyclopropanecarbonyl)imino)-4-((2-methoxy-3-(2-methyl-2H-tetrazol-5-yl)phenyl)amino)-N-(methyl-$d_3$)-1,6-dihydropyridine-3-carboxamide (0.100 g, 0.211 mmol) and DIPEA (0.221 mL, 1.266 mmol) in tetrahydrofuran (5 mL) at 0° C., 4-((bis(benzyloxy)phosphoryl)oxy)-3-methoxybenzoic acid (0.205 g, 0.211 mmol) was added. The mixture was stirred at RT for 3 h. The reaction mixture was concentrated in vacuum at 30° C. to give crude product as a brown gum. RP-HPLC purification (Preparative column: Sunfire C18 (150×19 mm; 5 micron), mobile phase A: 0.1% formic acid in water, mobile phase B: acetonitrile, flow rate: 18 mL/min, gradient: 0/10, 10/45) gave the title compound (0.040 g, 0.026 mmol, 12.26% yield) as an off white solid. LC-MS (ES): m/z=866.2 [M+H]$^+$ Step 4

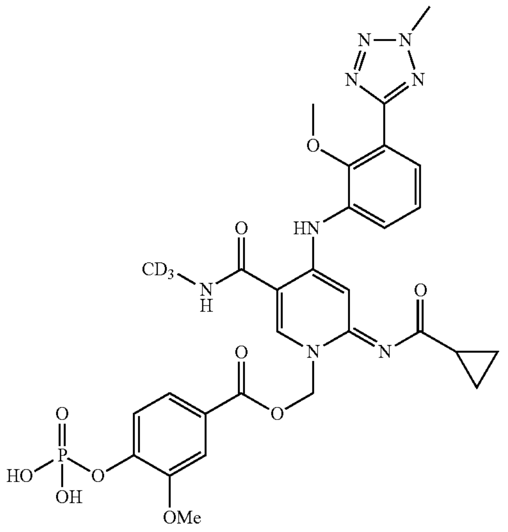

(E)-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1(2H)-yl)methyl 3-methoxy-4-(phosphonooxy)benzoate To a solution of (E)-(2-((cyclopropanecarbonyl)imino)-4-((2-methoxy-3-(2-methyl-2H-tetrazol-5-yl)phenyl)amino)-5-((methyl-$d_3$)carbamoyl)pyridin-1 (2H)-yl)methyl 4-((bis(benzyloxy)phosphoryl)oxy)-3-methoxybenzoate (0.070 g, 0.081 mmol) in 1,2-dichloroethane (2 mL), was added TFA (0.623 mL, 8.08 mmol) followed by anisole (0.442 mL, 4.04 mmol) at 0° C. The mixture was stirred at 50° C. for 2 h and subsequently concentrated under vacuum to give the crude product as a brown gum. RP-HPLC purification (Preparative column: Sunfire C18 (150×19 mm; 5 micron), mobile phase A: 0.1% formic acid in water, mobile phase B: acetonitrile, flow rate: 18 mL/min, gradient: 0/10, 10/35) gave the title compound (0.026 g, 0.038 mmol, 46.4% yield) as an off white solid. $^1$H NMR (400 MHz, DMSO-$d_6$) δ 0.66-0.81 (m, 4H), 1.71 (br. s, 1H), 3.74 (s, 3H), 3.81 (s, 3H), 4.46 (s, 3H), 6.27 (br. s, 2H), 7.38 (t, J=7.60 Hz, 1H), 7.48-7.56 (m, 3H), 7.61-7.68 (m, 1H), 7.71-7.86 (m, 2H), 8.74-8.93 (m, 2H), 11.01-11.03 (m, 1H); LC-MS (ES): m/z=686.2 [M+H]$^+$; HPLC RT and purity: 10.082 min and 99.31% (method A) &11.877 min and 98.83% (method B).

Example 6

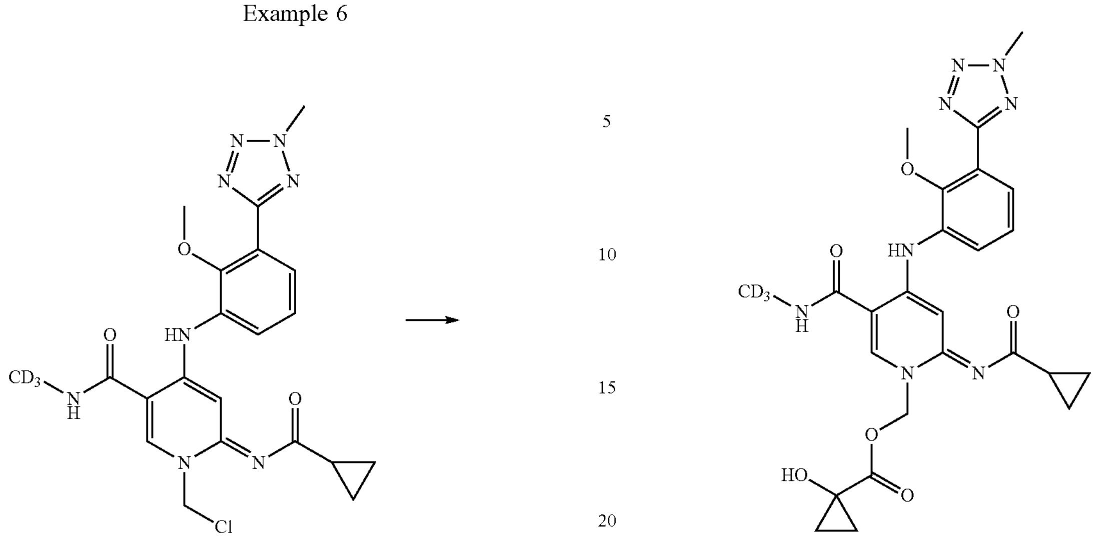

(E)-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1(2H)-yl) methyl 1-hydroxycyclopropane-1-carboxylate

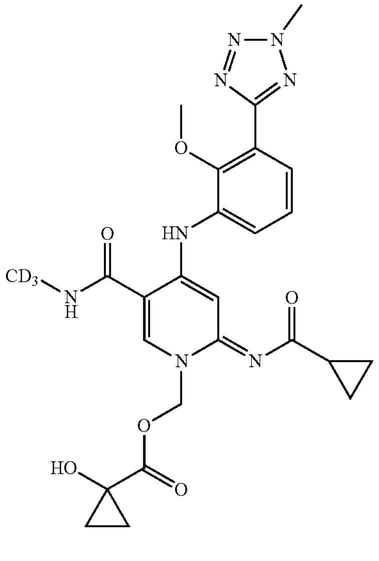

To a solution of (E)-1-(chloromethyl)-6-((cyclopropanecarbonyl)imino)-4-((2-methoxy-3-(2-methyl-2H-tetrazol-5-yl)phenyl)amino)-N-(methyl-$d_3$)-1,6-dihydropyridine-3-carboxamide (0.025 g, 0.032 mmol) and DIPEA (0.033 mL, 0.190 mmol) in tetrahydrofuran (2 mL) at 0° C., was added 1-hydroxycyclopropanecarboxylic acid (3.88 mg, 0.038 mmol). After being stirred at RT for 3 h, the reaction mixture was concentrated in vacuum at 30° C. to give the crude product. RP-HPLC purification (Preparative column: Sunfire (150×4.6 mm; 5 micron), mobile phase A: 0.1% formic acid in water, mobile phase B: acetonitrile, flow rate: 1.0 mL/min, gradient: 0/10, 20/100) gave the title compound (0.011 g, 0.019 mmol, 59.9% yield) as an off-white solid. $^1H$ NMR (400 MHz, DMSO-$d_6$) δ 0.86-0.94 (m, 4H), 1.04-1.09 (m, 2H), 1.19-1.24 (m, 2H), 2.07 (m, 1H), 3.74 (s, 3H), 4.46 (s, 3H), 6.19 (br. s, 2H), 6.42 (br. s, 1 H), 7.41-7.50 (m, 1H), 7.64 (s, 1H), 7.90 (br. s, 1H), 9.01 (br. s, 1H), 9.09 (br. s, 1H), 10.94 (br. s, 1H), 11.51 (br. s, 1H); LC-MS (ES): m/z=540.2 $[M+H]^+$; HPLC RT and purity: 10.047 min and 93.15% (method A) &12.826 min and 91.08% (method B).

Example 7

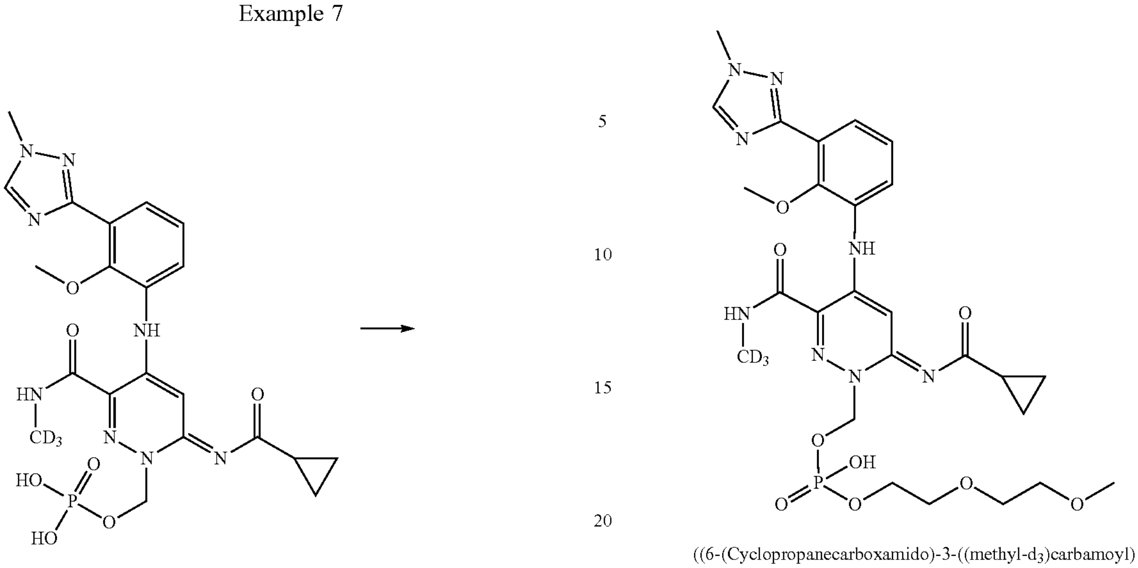

((6-(Cyclopropanecarboxamido)-3-((methyl-d3)carbamoyl) pyridazin-4-yl)(2-methoxy-3-(1-methyl-1H-1,2,4-triazol-3-yl)phenyl)amino)methyl (2-(2-methoxyethoxy)ethyl) hydrogen phosphate

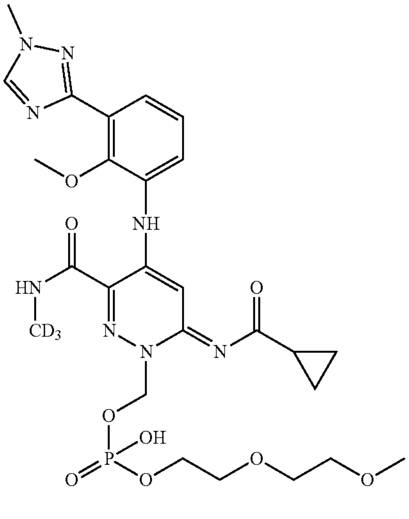

To a solution of ((6-(cyclopropanecarboxamido)-3-((methyl-$d_3$)carbamoyl)pyridazin-4-yl) (2-methoxy-3-(1-methyl-1H-1,2,4-triazol-3-yl)phenyl)amino)methyl dihydrogen phosphate (30 mg, 0.056 mmol, 1 equiv.) in DMF (0.5 mL), 2-(2-methoxyethoxy) ethanol (8.08 mg, 0.067 mmol, 1.200 equiv.), EDC (10.74 mg, 0.056 mmol) were added. The mixture was stirred at RT for 16 h. The crude product was purified using RP HPLC (Preparative column: Sunfire C18 (19×250 mm; 5 micron), mobile phase A: 10 mM ammonium acetate in water, mobile phase B: acetonitrile, flow rate: 18 mL/min, gradient: 0/20, 10/35). The fraction was concentrated using high vacuum at 30° C. The residue was dissolved in a mixture of acetonitrile and water. The resultant solution was frozen and lyophilized for 12 h to get the title compound (15.6 mg, 0.024 mmol, 43.4% yield) as a pale yellow solid. $^1$H NMR (400 MHz, $D_2O$) δ 8.43 (s, 1H), 7.83 (br. s, 1H), 7.68 (d, J=8.03 Hz, 1H), 7.49 (dd, J=8.03, 1.51 Hz, 1H), 7.34 (t, J=7.78 Hz, 1H), 6.03 (d, J=12.05 Hz, 2H), 3.92-3.98 (m, 5H), 3.55-3.63 (m, 7H), 3.48-3.52 (m, 2H), 3.29 (s, 3H), 1.91 (br.s, 1H), 0.98-1.02 (m, 4H). LC-MS (ES): m/z=638.2 $[M+H]^+$; HPLC RT and purity: 5.74 min and 99.51% (method A) δ 5.90 min and 99.44% (method B).

Example 8

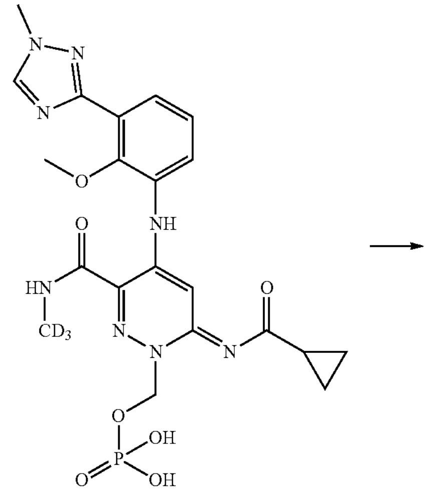

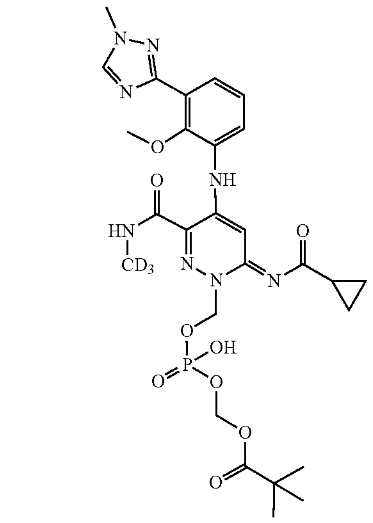

(E)-((((6-((Cyclopropanecarbonyl)imino)-4-((2-methoxy-3-(1-methyl-1H-1,2,4-triazol-3-yl)phenyl)amino)-3-((methyl-$d_3$)carbamoyl)pyridazin-1(6H)-yl)methoxy)(hydroxy)phosphoryl)oxy)methyl pivalate

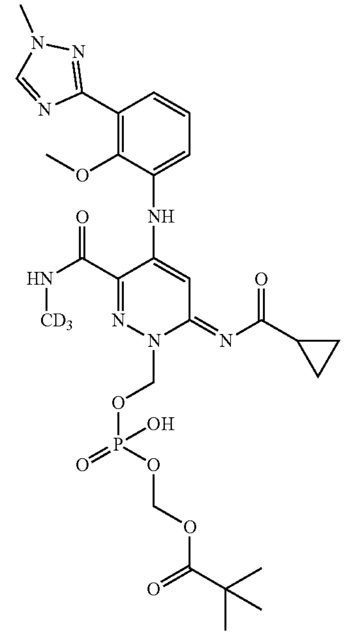

To a solution of (E)-(6-((cyclopropanecarbonyl)imino)-4-((2-methoxy-3-(1-methyl-1H-1,2,4-triazol-3-yl)phenyl)amino)-3-((methyl-$d_3$)carbamoyl)pyridazin-1 (6H)-yl) methyl dihydrogen phosphate (60 mg, 0.112 mmol, 3 equiv.) in DMF (1 mL), DIPEA (0.059 mL, 0.336 mmol), and iodomethylpivalate (81 mg, 0.336 mmol) were added. The reaction mixture was stirred at RT for 16 h. The reaction mixture was directly purified using RP HPLC (Preparative column: Kinetex (21.2×150 mm; 5 micron), mobile phase A: 0.1% formic acid, mobile phase B: acetonitrile, flow rate: 20 mL/min.). The fraction was concentrated using high vacuum at 30° C. The residue was dissolved in a mixture of acetonitrile and water, frozen and lyophilized for 12 h to get the title compound (9.42 mg, 0.014 mmol, 12.37% yield) as a pale yellow solid. $^1$H NMR (400 MHz, $D_2O$) δ 8.38 (s, 1H), 7.77 (s, 1H), 7.70 (d, J=7.72 Hz, 1H), 7.45 (dd, J=7.97, 1.51 Hz, 1H), 7.33-7.38 (m, 1H), 6.05 (d, J=13.11 Hz, 2H), 5.41 (d, J=13.55 Hz, 2H), 3.97 (s, 3H), 3.51 (s, 3H), 1.82 (bs, 1H), 1.07 (s, 9H), 0.93-1.01 (m, 4H). LC-MS (ES): m/z=650.2 $[M+H]^+$; HPLC RT and purity: 7.045 min and 95.58% (method A) &6.85 min and 95.71% (method B).

Example 9

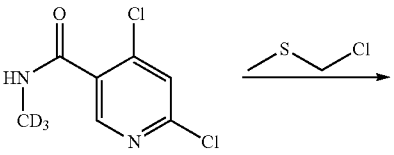

-continued

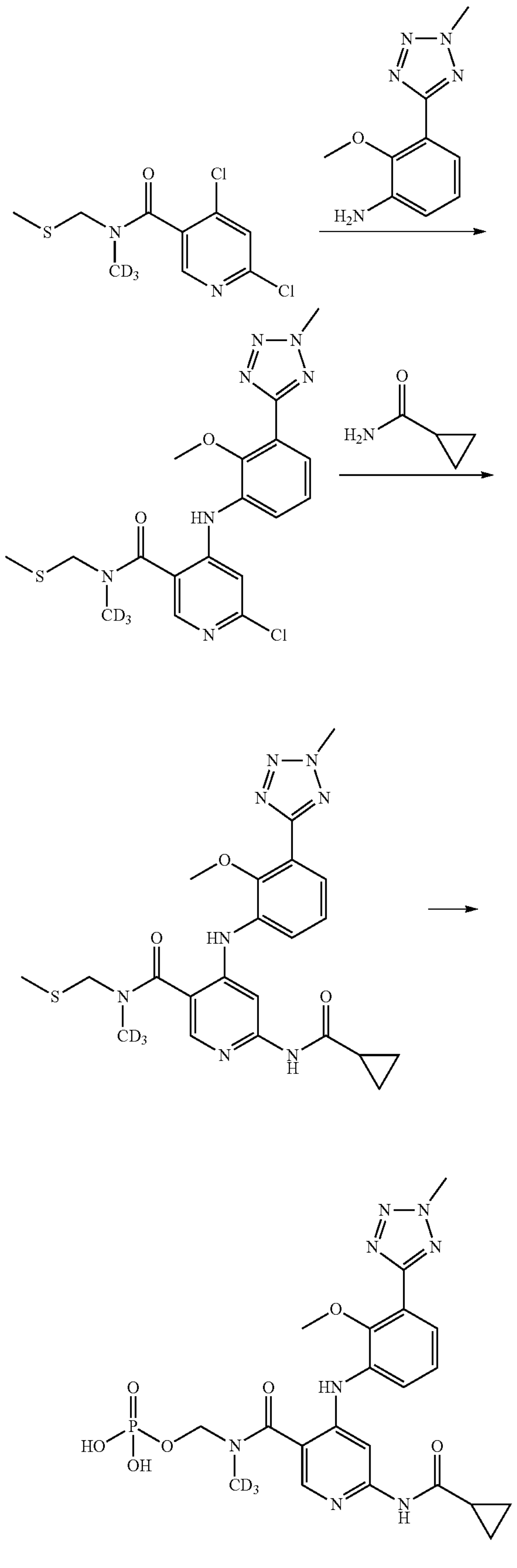

Step 1

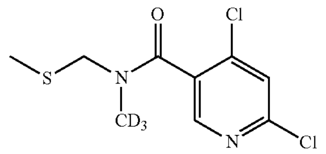

4, 6-Dichloro-N-(methyl-d3)-N-((methylthio)methyl)nicotinamide

To a stirred solution of 4,6-dichloro-N-(methyl-$d_3$) nicotinamide (450 mg, 2.163 mmol) in anhydrous DMF (10 mL) at 0° C., was added NaH (112 mg, 2.81 mmol). The mixture was stirred for 1 h. Chloromethyl methyl sulfide (230 mg, 2.379 mmol) was added and the reaction mixture was brought to room temperature and stirred for 16 h. The reaction mixture was diluted with water (10 mL) and extracted with ethyl acetate (2×50 mL). The organic layer was washed with $H_2O$ (1×10 mL) and saturated NaCl (1×10 mL), dried over anhydrous $Na_2SO_4$, filtered and concentrated under reduced pressure. The crude product was purified using CombiFlash (40 g silica gel column; pet. ether: ethyl acetate as eluent). The desired product was eluted using 15% ethyl acetate in pet. ether. The desired fractions were evaporated under reduced pressure to afford the title compound (350 mg, 1.109 mmol, 46.2% yield) as a brown oil. $^1$H NMR (300 MHz, DMSO-$d_6$) δ 2.17 (s, 3H), 4.37 (s, 1H), 4.68 (br. s 1H), 7.96 (d, J=10.80 Hz, 1H), 8.48 (d, J=6.90 Hz, 1H). LC-MS (ES): m/z=268.0 $[M+H]^+$ Step 2

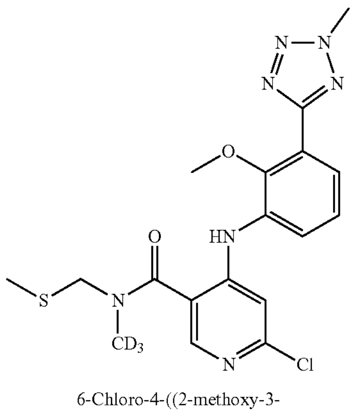

6-Chloro-4-((2-methoxy-3-(2-methyl-2H-tetrazol-5-yl)phenyl)amino)-N-(methyl-d3)-N-((methylthio)methyl)nicotinamide To a stirred solution of 2-methoxy-3-(2-methyl-2H-tetrazol-5-yl) aniline (260 mg, 1.267 mmol) and 4,6-dichloro-N-(methyl-$d_3$)-N-((methylthio)methyl) nicotinamide (340 mg, 1.267 mmol) in anhydrous THF (10 mL), was added drop-wise 1M LiHMDS in THF (3.17 mL, 3.17 mmol) at room temperature. After being stirred for 1 h, the reaction mixture was cooled to 0° C., quenched with saturated ammonium chloride solution (50 mL), and extracted with ethyl acetate (2×50 mL). The organic layer was washed with $H_2O$ (1×30 mL), and saturated NaCl solution (1×30 mL). The organic layer was dried over anhydrous $Na_2SO_4$, filtered and concentrated under reduced pressure to afford the title compound (550 mg, 1.032 mmol, 81% yield) as a brown semi solid. LC-MS (ES): m/z=437.2 $[M+H]^+$ Step 3

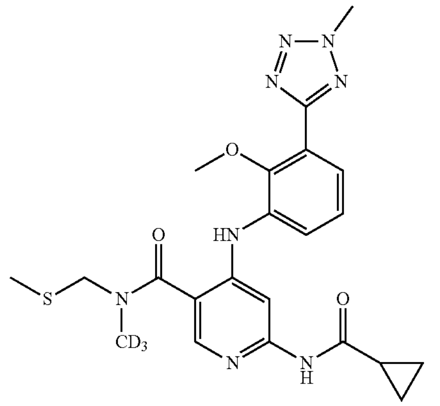

6-(Cyclopropanecarboxamido)-4-((2-methoxy-3-(2-methyl-2H-tetrazol-5-yl)phenyl)amino)-N-(methyl-$d_3$)-N-((methylthio)methyl)nicotinamide In a sealed tube, a stirred suspension of 6-chloro-4-((2-methoxy-3-(2-methyl-2H-tetrazol-5-yl)phenyl)amino)-N-(methyl-$d_3$)-N-((methylthio)methyl) nicotinamide (550 mg, 1.259 mmol), cyclopropanecarboxamide (118 mg, 1.385 mmol), $Cs_2CO_3$ (1230 mg, 3.78 mmol), xantphos (146 mg, 0.252 mmol) and $Pd_2(dba)_3$ (115 mg, 0.126 mmol) in anhydrous dioxane (10 mL), was purged with nitrogen gas and then sealed. The mixture was stirred at 110° C. for overnight. The reaction mixture was allowed to cool to room temperature and diluted with ethyl acetate (25 mL). The black suspension was filtered through celite bed and the bed was washed with ethyl acetate (50 mL). The filtrate was concentrated under reduced pressure to afford the crude product as a black semi-solid. The residue was purified using CombiFlash (40 g silica gel column; MeOH: chloroform as eluent). The desired product was eluted using 4% MeOH in chloroform. The desired fractions were evaporated under reduced pressure to afford the title compound (500 mg, 0.875 mmol, 69.5% yield) as a yellow solid. $^1H$ NMR (400 MHz, DMSO-$d_6$) δ 0.63-0.77 (m, 4H), 1.97-1.99 (m, 1H), 2.07 (br. s, 3H), 3.70 (s, 3H), 4.45 (s, 3H), 4.67 (s, 2H), 7.32 (t, J=7.78 Hz, 1H), 7.60-7.63 (m, 2H), 8.00 (s, 1H), 8.16 (s, 1H), 8.48-8.51 (m, 1H), 10.76 (s, 1H); LC-MS (ES): m/z=486.2 $[M+H]^+$ Step 4

(6-(Cyclopropanecarboxamido)-4-((2-methoxy-3-(2-methyl-2H-tetrazol-5-yl)phenyl)amino)-N-(methyl-$d_3$)nicotinamico)methyl dihydrogen phosphate

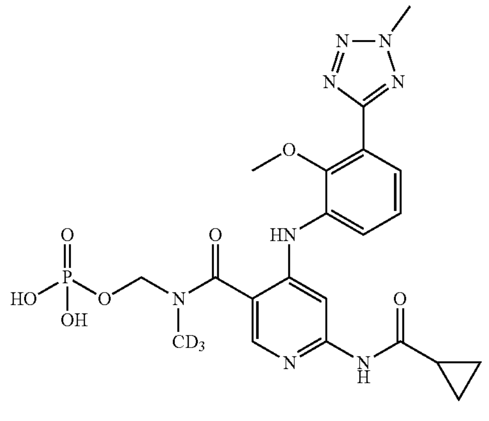

To a stirred solution of 6-(cyclopropanecarboxamido)-4-((2-methoxy-3-(2-methyl-2H-tetrazol-5-yl)phenyl)amino)-N-(methyl-$d_3$)-N-((methylthio)methyl) nicotinamide (100 mg, 0.206 mmol) in anhydrous THF (5 mL), was added powdered molecular sieves (15 mg) and NIS (93 mg, 0.412 mmol). The reaction mixture was stirred for 5 min at room temperature and added phosphoric acid (605 mg, 6.18 mmol) in one portion. The reaction mixture was stirred for 5 min. and cooled to 0° C. MeOH (1 mL) was added and then pH was adjusted to approximately 8 by adding saturated $Na_2CO_3$ solution. The reaction mixture was filtered through celite bed and the bed was washed with THF (20 mL). The filtrate was concentrated under high vacuum at 30° C. to get the crude product as semi-solid. The crude compound was purified in reverse phase prep-HPLC (Preparative column: INERTSIL ODS (250×19 mm; 3.5 micron), mobile phase A: water, mobile phase B: acetonitrile, flow rate: 17 mL/min, gradient: 0/0, 12/20). The prep fraction containing the desired product was concentrated under high vacuum at 30° C. The residue was dissolved in a mixture of acetonitrile and water and the solution was lyophilized for 24 h to afford the title compound (40 mg, 0.068 mmol, 33.1% yield) as an off-white solid. $^1H$ NMR (400 MHz, $D_2O$) δ 0.89-0.98 (m, 4H), 1.83 (m, 1H), 3.63-3.67 (m, 3H), 4.45-4.49 (m, 3H), 5.04-5.13 (m, 2H), 7.36-7.46 (m, 1H), 7.54-7.63 (m, 2H), 7.71-7.81 (m, 1H), 8.24-8.31 (m, 1H). LC-MS (ES): m/z=536.2 $[M+H]^+$; HPLC RT and purity: 5.918 min and 99.73% (method A) δ 5.748 min and 99.68% (method B).

Example 10

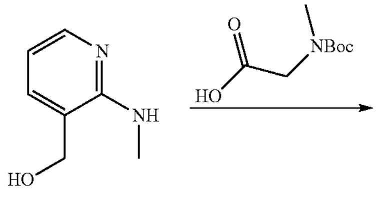

-continued

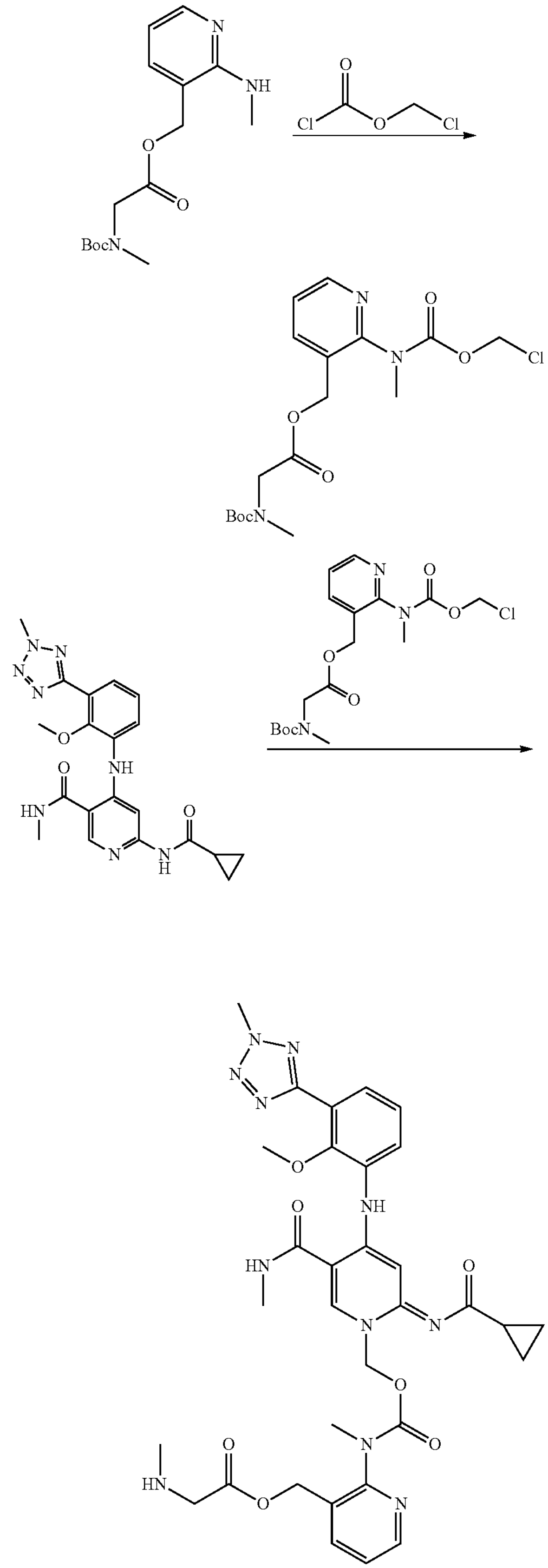

Step 1

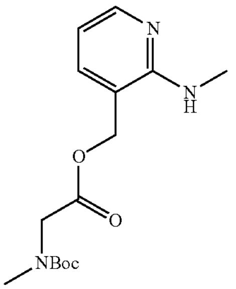

(2-(Methylamino)pyridin-3-yl) methyl-N-(tert-butoxycarbonyl) -N-methylglycinate

To a stirred solution of (2-(methylamino)pyridin-3-yl) methanol (100 mg, 0.724 mmol) in anhydrous DCM (2 mL), were added 2-((tert-butoxycarbonyl)(methyl)amino) acetic acid (137 mg, 0.724 mmol), EDC (180 mg, 0.941 mmol) and finally DMAP (88 mg, 0.724 mmol). The reaction mixture was stirred for 16 h at room temperature and then was diluted with water and extracted with DCM. The organic layer was washed with $H_2O$, and saturated NaCl, dried over anhydrous $Na_2SO_4$, filtered and concentrated under reduced pressure. The residue was purified using CombiFlash (12 g silica gel column; 40% ethyl acetate in pet. ether) to afford the title compound (210 mg, 0.563 mmol, 78% yield) as a brown semi-solid. $^1$H NMR (400 MHz, DMSO-$d_6$) δ 1.16-1.40 (m, 9H), 2.82-2.87 (m, 6H), 4.00 (m, 2H), 4.99 (d, J=14.56 Hz, 2H), 6.18 (br. s, 1H), 6.51 (dd, J=7.03, 5.02 Hz, 1H), 7.37-7.43 (m, 1H), 8.03 (dd, J=5.02, 1.51 Hz, 1H); LC-MS (ES): m/z=310.2 $[M+H]^+$ Step 2

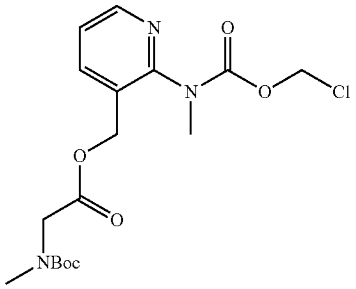

(2-(((Chloromethoxy)carbonyl) (methyl)amino)pyridin-3-yl) methyl N-(tert-butoxycarbonyl) -N-methylglycinate To a stirred solution of (2-(methylamino)pyridin-3-yl) methyl 2-((tert-butoxycarbonyl)(methyl)amino)acetate (220 mg, 0.711 mmol) in anhydrous DCM (3 mL) at 0° C., was added DIPEA (0.621 mL, 3.56 mmol) followed by drop-wise addition of chloromethyl chloroformate (275 mg, 2.133 mmol). The reaction mixture was allowed to warm to room temperature and stirred for 3 h. The reaction mixture was cooled to 0° C., treated with saturated sodium bicarbonate solution and extracted with DCM. The organic layer was washed with $H_2O$ and saturated NaCl, dried over anhydrous $Na_2SO_4$, filtered and concentrated under reduced pressure. The residue was purified using CombiFlash (12 g silica gel column; 30% ethyl acetate in pet. ether) to afford the title compound (200 mg, 0.428 mmol, 60.2% yield) as a yellow semi-solid. LC-MS (ES): m/z=402.2 $[M+H]^+$ Step 3

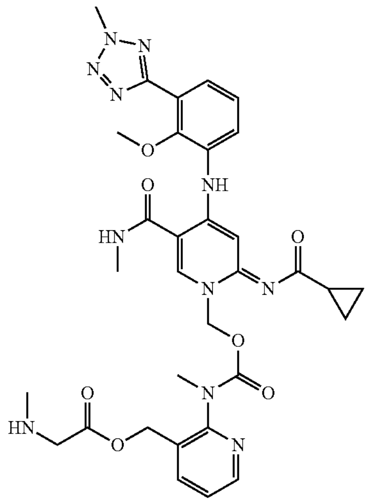

(E)-(2-((((2-((Cyclopropanecarbonyl)imino)-4-((2-methoxy-3-(2-methyl-2H-tetrazol-5-yl)phenyl)amino)-5-(methylcarbamoyl)pyridin-1(2H)-yl)methoxy)carbonyl)(methyl)amino)pyridin-3-yl)methyl methylglycinate trifluoroacetic acetate To a stirred solution of 6-(cyclopropanecarboxamido)-4-((2-methoxy-3-(2-methyl-2H-tetrazol-5-yl)phenyl)amino)-N-methylnicotinamide (150 mg, 0.355 mmol) in anhydrous acetonitrile (2.5 mL), were added $K_2CO_3$ (147 mg, 1.065 mmol), (2-(((chloromethoxy)carbonyl)(methyl)amino)pyridin-3-yl)methyl 2-((tert-butoxycarbonyl)(methyl)amino)acetate (428 mg, 1.065 mmol) and subsequently sodium iodide (186 mg, 1.243 mmol). The reaction mixture was heated to 80° C. and stirred for 30 h under nitrogen. The reaction mixture was diluted with water and extracted with ethyl acetate. The organic layer was washed with $H_2O$ and saturated NaCl, dried over anhydrous $Na_2SO_4$, filtered and concentrated under reduced pressure to afford the crude compound as a mixture of mono-alkylated and di-alkylated products as brown semi solid. To this crude mixture (400 mg, 0.170 mmol) in anhydrous DCM (5 mL), was added 4 M HCl in dioxane (5 mL, 20.00 mmol) at 0° C. After being stirred for 15 min, the reaction mixture was concentrated to dryness. The crude compound was purified by reverse phase prep-HPLC (Preparative column: Symmetry C8 (300×19 mm; 7 micron), mobile phase A: 0.1% TFA in water, mobile phase B: acetonitrile, flow rate: 18 mL/min, gradient: 0/10, 5/20). The prep fractions were concentrated under high vacuum at 30° C. The residue was dissolved in a mixture of acetonitrile and water and the solution was lyophilized to afford the title compound (20 mg, 0.024 mmol, 13.94% yield) as an off-white solid. $^1H$ NMR (400 MHz, MeOH-$d_4$) δ 0.95-1.02 (m, 4H) 1.92-2.02 (m, 1H) 2.77 (s, 3H) 2.99 (s, 3H) 3.37-3.45 (m, 3H) 3.84 (s, 3H) 4.04-4.11 (m, 2H) 4.49 (s, 3H) 5.14-5.34 (m, 2H) 6.09-6.38 (m, 2H) 7.42-7.56 (m, 2H) 7.65-7.80 (m, 2H) 7.99-8.09 (m, 2H) 8.45-8.57 (m, 1H) 8.70-8.94 (m, 1H). LC-MS (ES): m/z=688.2 $[M+H]^+$; HPLC RT and purity: 8.827 min and 99.49% (method A) δ 11.610 min and 95.18% (method B).

Example 11

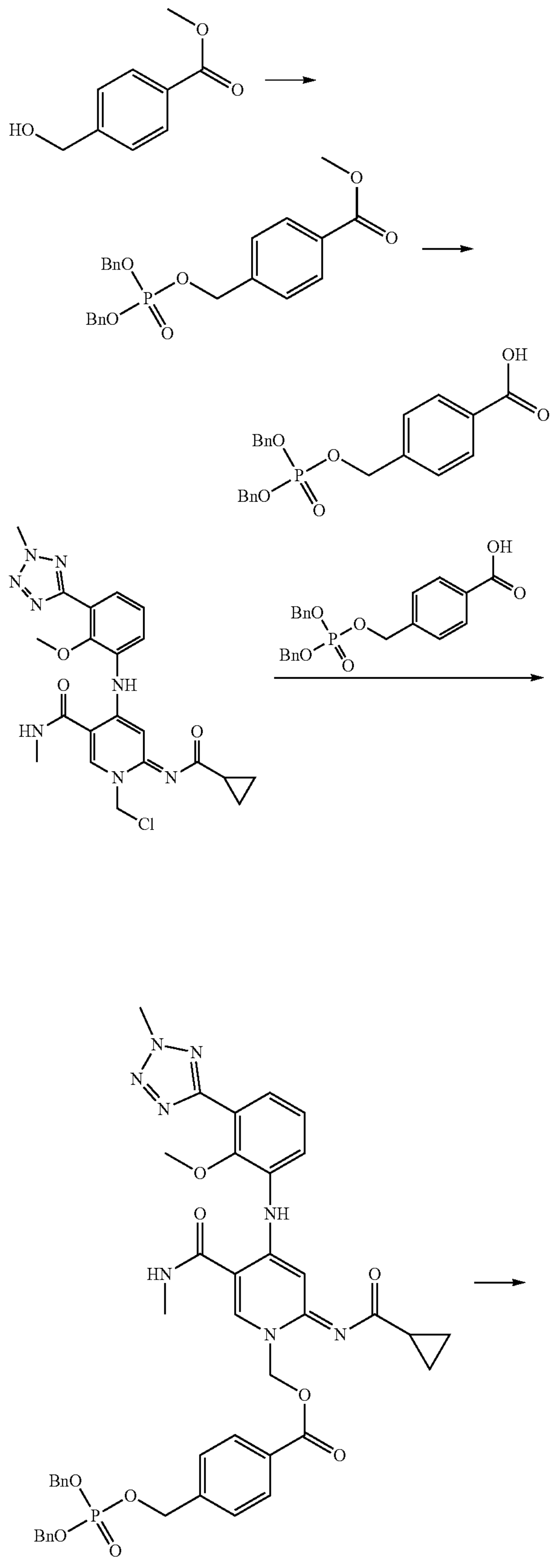

-continued

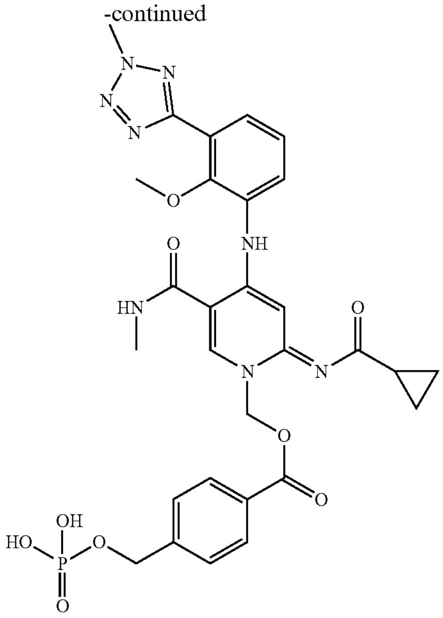

Step 1

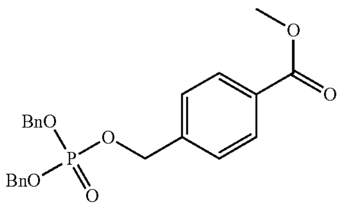

Methyl 4-(((bis(benzyloxy)phosphoryl)oxy)methyl)benzoate

To a stirred solution of methyl 4-(hydroxymethyl)benzoate (2 g, 12.04 mmol) and tetrazole (27.3 g, 24.07 mmol) in acetonitrile, was added dibenzyldiisopropyl phosphoramidite (4.16 g, 12.04 mmol) at room temperature. After being stirred for 16 h, the reaction mixture was cooled to 0° C., and $H_2O_2$ (2.108 mL, 24.07 mmol) was added drop-wise. After being stirred for 20 min at 0° C., the mixture was quenched with saturated sodium bicarbonate solution and extracted with EtOAc. The organic layer was washed with $H_2O$, and saturated NaCl. The organic layer was dried over anhydrous $Na_2SO_4$, filtered and concentrated under reduced pressure. The residue was purified using CombiFlash (40 g silica gel column; 25% ethyl acetate in pet. ether as eluent). The desired fractions were evaporated under reduced pressure to afford the title compound (3.0 g, 5.63 mmol, 46.8% yield) as a brown semi-solid. $^1H$ NMR (300 MHz, $CDCl_3$) δ 3.92 (s, 3H), 4.99-5.08 (m, 6H), 7.29-7.38 (m, 10H), 7.42 (dd, J=5.70, 7.50 Hz, 2H), 7.45-8.05 (m, 2H).

Step 2

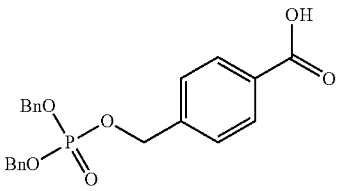

4-(((Bis(benzyloxy)phosphoryl)oxy)methyl)benzoic acid

To a stirred solution of methyl 4-(((bis(benzyloxy)phosphoryl)oxy)methyl)benzoate (1 g, 2.345 mmol) in THF (10 mL) at 0° C., was added a solution of LiOH (0.112 g, 4.69 mmol) in water (10 mL) drop-wise. The reaction mixture was allowed to warm to RT and stirred for 16 h. The mixture was cooled to 0° C. and treated with 1.5N HCl solution (20 mL) and extracted with EtOAc. The organic layer was washed with $H_2O$ and saturated NaCl, dried over anhydrous $Na_2SO_4$, filtered and concentrated under reduced pressure to afford the title compound (600 mg, 0.757 mmol, 32.3% yield) as a brown solid. The crude product was used as such. $^1H$ NMR (400 MHz, MeOH-$d_4$) □ 8.02 (d, J=8.00 Hz, 2H), 7.48 (d, J=8.0 Hz, 2H), 7.42-7.32 (m, 10H), 5.10-5.04 (m, 4H), 4.70 (s, 2H).

Step 3

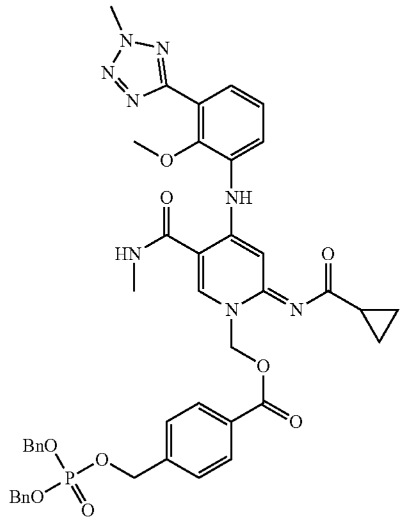

(E)-(2-((Cyclopropanecarbonyl)imino)-4-((2-methoxy-3-(2-methyl-2H-tetrazol-5-yl)phenyl)amino)-5-(methylcarbamoyl)pyridin-1(2H)-yl) methyl 4-(((bis(benzyloxy)phosphoryl)oxy)methyl)benzoate To a stirred solution of (E)-1-(chloromethyl)-6-((cyclopropanecarbonyl)imino)-4-((2-methoxy-3-(2-methyl-2H-tetrazol-5-yl)phenyl)amino)-N-methyl-1,6-dihydropyridine-3-carboxamide (50 mg, 0.106 mmol) in anhydrous THF (2.5 mL) at 0° C., was added DIPEA (0.037 mL, 0.212 mmol) followed by 4-(((bis(benzyloxy)phosphoryl)oxy)methyl)benzoic acid (43.8 mg, 0.106 mmol). The reaction mixture was stirred for 2 h at 0° C. Then the mixture was diluted with water (5 mL) and extracted with ethyl acetate (2×25 mL). The organic layer was washed with $H_2O$ (1×10 mL), and saturated NaCl (1×10 mL). The organic layer was dried over anhydrous $Na_2SO_4$, filtered and concentrated under reduced pressure. The crude compound was purified in reverse phase prep-HPLC (Preparative column: SUNFIRE C18 (150×19 mm; 5 micron), mobile phase A: 10 mM ammonium acetate in water, mobile phase B: acetonitrile, flow rate: 18 mL/min, gradient: 0/30, 10/70). The prep fraction containing the desired product was concentrated under high vacuum at 30° C. The residue was dissolved in a mixture of acetonitrile and water, and lyophilized for 24 h to afford the title compound (20 mg, 0.023 mmol, 21.80% yield) as an off-white solid. $^1$H NMR (400 MHz, MeOH-$d_4$) δ 0.69-714 (m, 2H), 0.91-093 (m, 2H), 1.61-1.7 (m, 1H), 2.94 (s, 3H), 3.82 (s, 3H), 4.45 (s, 3H), 5.02 (s, 2H), 5.05 (s, 2H), 5.07 (s, 2H), 6.32 (s, 2H), 7.31-7.40 (m, 11H), 7.40 (d, J=9.04 Hz, 3H), 7.70 (d, J=7.53 Hz, 1H), 7.79 (s, 2H), 7.99 (d, J=8.03 Hz, 2H), 8.52 (s, 1H); LC-MS (ES): m/z=847.2 $[M+H]^+$ Step 4

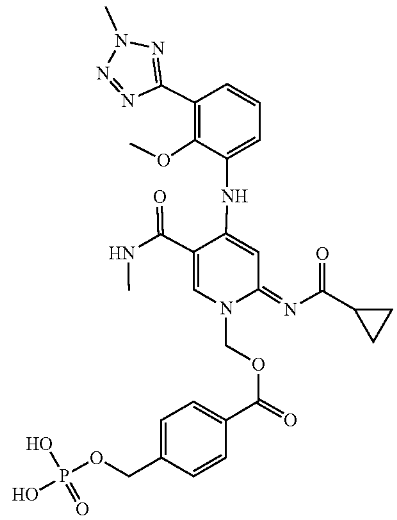

(E)-(2-((Cyclopropanecarbonyl)imino)-4-((2-methoxy-3-(2-methyl-2H-tetrazol-5-yl)phenyl)amino)-5-(methylcarbamoyl)pyridin-1(2H)-yl)methyl 4-((phosphonooxy)methyl)benzoate To a stirred solution of (E)-(2-((cyclopropanecarbonyl)imino)-4-((2-methoxy-3-(2-methyl-2H-tetrazol-5-yl)phenyl)amino)-5-(methylcarbamoyl)pyridin-1 (2H)-yl)methyl 4-(((bis(benzyloxy)phosphoryl)oxy)methyl)benzoate (20 mg, 0.024 mmol) in anhydrous DCE (0.7 mL), was added anisole (2.58 μL, 0.024 mmol) followed by TFA (1.820 μL, 0.024 mmol). The reaction mixture was heated to 50° C. and stirred for 16 h. The mixture was concentrated to dryness under high vacuum. The crude compound was purified in reverse phase prep-HPLC (Preparative column: Xbridge phenyl (250×19 mm; 5 micron), mobile phase A: 0.1% Formic acid in water, mobile phase B: acetonitrile, flow rate: 18 mL/min, gradient: 0/20, 6/30). The prep fraction containing the desired product was concentrated under high vacuum at 30° C. The residue was dissolved in a mixture of acetonitrile and water, which was lyophilized for 24 h to afford the title compound (10 mg, 0.015 mmol, 62.2% yield) as an off white solid. $^1$H NMR (400 MHz, DMSO-$d_6$) δ 0.55-0.74 (m, 4H), 1.45-1.51 m, 1H), 2.82 (d, J=4.52 Hz, 3H), 3.75 (br. s, 3H), 4.46 (s, 3H), 4.96 (d, J=7.53 Hz, 2H), 6.26 (br. s, 2H), 7.37 (br. s, 1H), 7.54 (d, J=8.53 Hz, 2H), 7.64 (br. s, 1H), 7.70 (br. s, 1H), 7.92 (br. s, 1H), 7.97 (d, J=8.03 Hz, 2H), 8.65 (s, 1H), 8.73 (br. s, 1H), 10.77 (br. s, 1H); LC-MS (ES): m/z=667.2 $[M+H]^+$; HPLC RT and purity: 4.675 min and 98.23% (method A) δ 6.088 min and 98.58% (method B).

Example 12

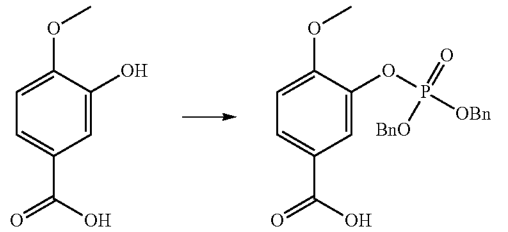 [SMILES: COc1ccc(C(=O)O)cc1O ; COc1ccc(C(=O)O)cc1OP(=O)(OCc1ccccc1)OCc1ccccc1]

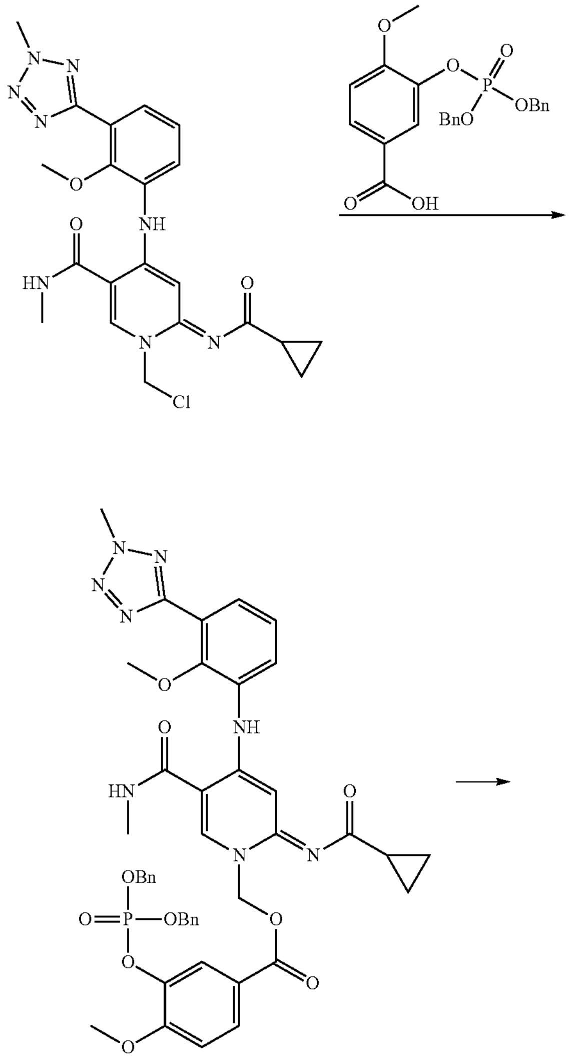

-continued

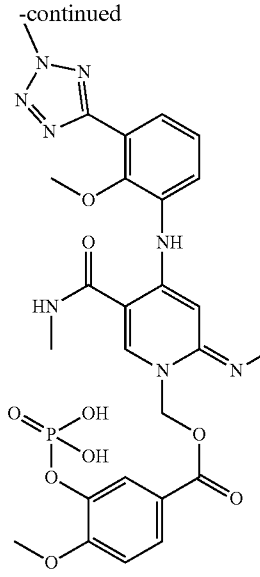

Step 1

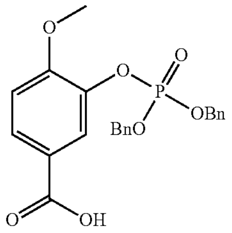

3-((Bis(benzyloxy)phosphoryl)oxy)-4-methoxybenzoic acid

To a stirred solution of 3-hydroxy-4-methoxybenzoic acid (300 mg, 1.784 mmol) in anhydrous acetonitrile (10 mL) at 0° C., was added 1H-tetrazole (91 mg, 2.68 mmol) followed by dibenzyldiisopropylphosphoramidite (678 mg, 1.963 mmol) drop-wise. After the addition, the reaction mixture was brought to room temperature and stirred for 16 h. The mixture was cooled to 0° C., and $H_2O_2$ (0.312 mL, 3.57 mmol) was added drop-wise. After stirring for 20 min, the reaction mixture was extracted with ethyl acetate (2×25 mL). The organic layer was washed with $H_2O$ (1×10 mL) and saturated NaCl (1×10 mL), dried over anhydrous $Na_2SO_4$, filtered and concentrated under reduced pressure. The crude compound was purified in reverse phase prep-HPLC. (Preparative column: SUNFIRE C18 (150×19 mm; 5 micron), mobile phase A: 0.1% formic acid in water, mobile phase B: acetonitrile, flow rate: 18 mL/min, gradient: 0/10, 10/55). The prep fraction containing the desired product was concentrated under high vacuum at 30° C. to afford the title compound (350 mg, 0.809 mmol, 45.3% yield) as a pale yellow oil. 1H NMR (300 MHz, DMSO-$d_6$) δ 3.85 (s, 3H), 5.16 (s, 2H), 5.19 (s, 2H), 7.22 (d, J=8.31 Hz, 1H), 7.75-7.77 (m, 10H), 7.80 (d, J=8.69 Hz, 2H), 12.88 (br. s, 1H); LC-MS (ES): m/z=429.0 $[M+H]^+$ Step 2

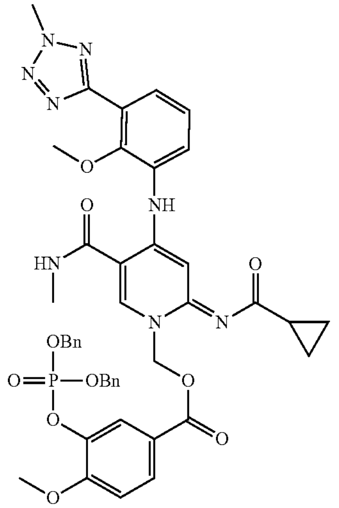

(E)-2(2-((Clyclopropanecarbonyl)imino)-4-((2-methoxy-3-(2-methyl-2H-tetrazol-5-yl)phenyl)amino)-5-(methylcarbamoyl)pyridin-1(2H)-yl)methyl 3-((bis(benzyloxy)phosphoryl)oxy)-4-methoxybenzoate To a stirred solution of (E)-1-(chloromethyl)-6-((cyclopropanecarbonyl)imino)-4-((2-methoxy-3-(2-methyl-2H-tetrazol-5-yl)phenyl)amino)-N-methyl-1,6-dihydropyridine-3-carboxamide (30 mg, 0.064 mmol) in anhydrous THF (2.5 mL) at 0° C., was added DIPEA (0.1 mL, 0.573 mmol) followed by 3-((bis(benzyloxy)phosphoryl)oxy)-4-methoxybenzoic acid (30.0 mg, 0.070 mmol). The reaction mixture was stirred for 2 h at 0° C. The mixture was diluted with water (10 mL) and extracted with ethyl acetate (2×25 mL). The organic layer was washed with $H_2O$ (1×10 mL), and saturated NaCl (1×10 mL). The organic layer was dried over anhydrous $Na_2SO_4$, filtered and concentrated under reduced pressure to afford the title compound (80 mg, 0.046 mmol, 72.8% yield) as a brown semi-solid. The crude product was used as such in the next reaction. LC-MS (ES): m/z=863.5 $[M+H]^+$ Step 3

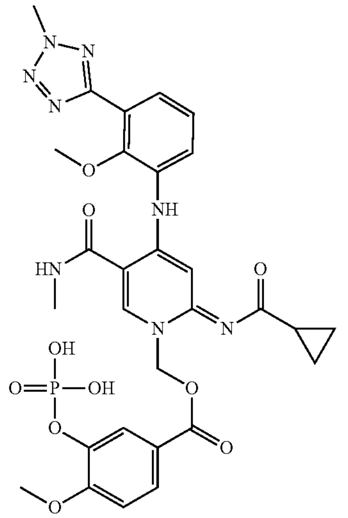

(E)-(2-((Clyclopropanecarbonyl)imino)-4-((2-methoxy-3-(2-methyl-2H-tetrazol-5-yl)phenyl)amino)-5-(methylcarbamoyl)pyridin-1(2H)-yl)methyl 4-methoxy-3-(phosphonooxy)benzoate To a stirred solution of (E)-(2-((cyclopropanecarbonyl)imino)-4-((2-methoxy-3-(2-methyl-2H-tetrazol-5-yl)phenyl)amino)-5-(methylcarbamoyl)pyridin-1 (2H)-yl)methyl 3-((bis(benzyloxy)phosphoryl)oxy)-4-methoxybenzoate (80 mg, 0.046 mmol) in anhydrous DCE (2.5 mL), was added anisole (0.1 mL, 0.915 mmol) and then TFA (0.2 mL, 2.60 mmol) at room temperature. The reaction mixture was heated to 50° C. and stirred for 16 h. The reaction mixture was concentrated to dryness under high vacuum. The crude compound was purified in reverse phase prep-HPLC. (Preparative column: Kinetex C18 (150×19 mm; 5 micron), mobile phase A: 0.1% formic acid in water, mobile phase B: acetonitrile, flow rate: 18 mL/min, gradient: 0/10, 10/35). The prep fraction containing the desired product was concentrated under high vacuum at 30° C. The residue was dissolved in a solvent mixture of acetonitrile and water and the solution was lyophilized for 24 h to afford the title compound (10 mg, 0.014 mmol, 31.0% yield) as an off-white solid. $^1$H NMR (400 MHz, DMSO-$d_6$) δ 0.80-0.82 (m, 4H), 1.99-2.00 (m, 1H), 2.83 (d, J=4.52 Hz, 3H), 3.75 (s, 3H), 3.86 (s, 3H), 4.46 (s, 3H), 6.38 (br. s, 2H), 7.03-7.45 (m, 4H), 7.66-7.73 (m, 2H), 7.84 (br. s, 1H), 8.03 (s, 1H), 9.03-9.24 (m, 1H), 11.35 (br. s, 1H); LC-MS (ES): m/z=683.2 [M+H]$^+$; HPLC RT and purity: 10.551 min and 98.75% (method A) δ 12.137 min and 98.30% (method B).

Example 13

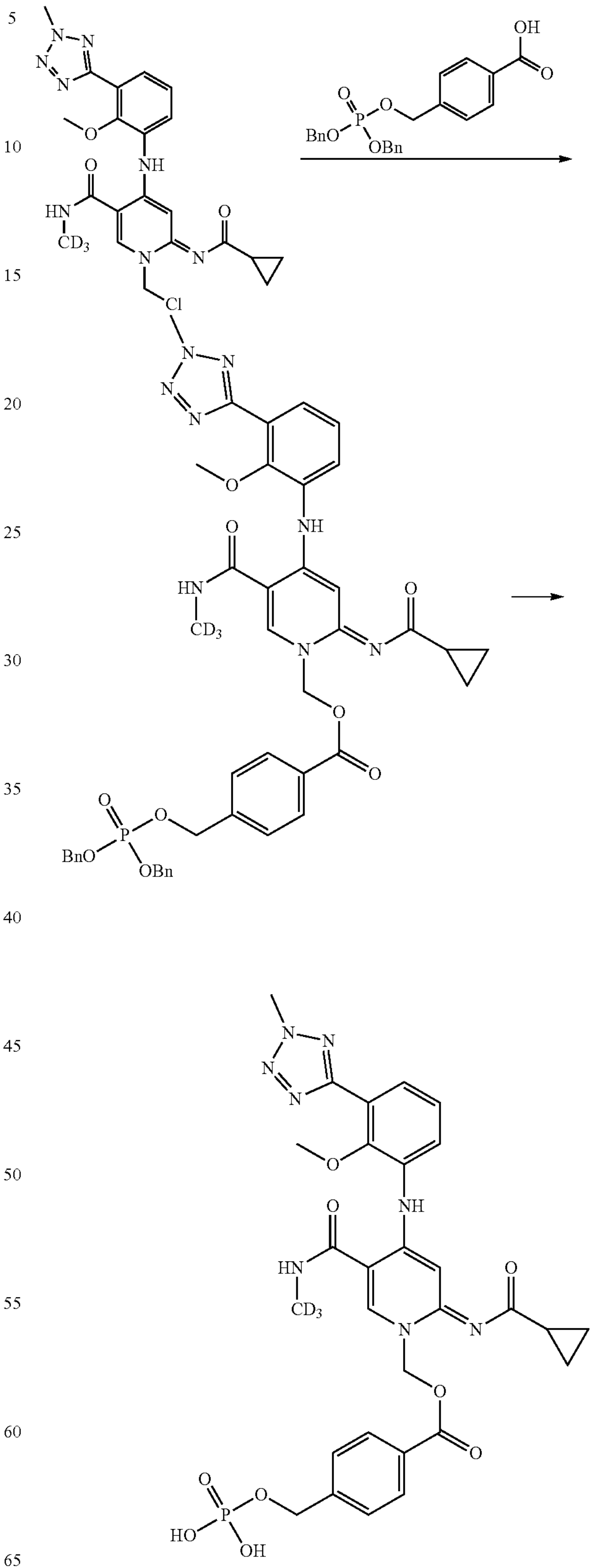

Step 1

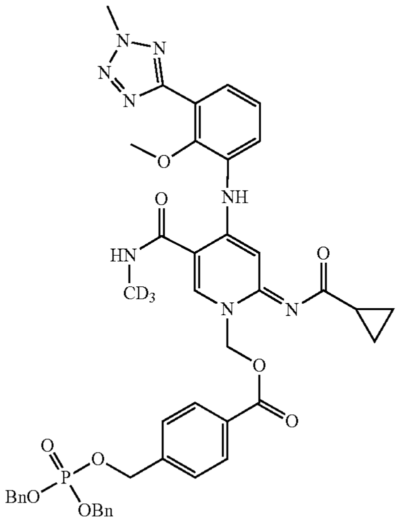

(E)-(2-((Cyclopropanecarbonyl)imino)-4-((2-methoxy-3-(2-methyl-2H-tetrazol-5-yl)phenyl)amino)-5-((methyl-d3)carbamoyl)pyridin-1(2H)-yl)methyl 4-(((bis(benzyloxy)phosphoryl)oxy)methyl)benzoate To a stirred solution of (E)-1-(chloromethyl)-6-((cyclopropanecarbonyl)imino)-4-((2-methoxy-3-(2-methyl-2H-tetrazol-5-yl)phenyl)amino)-N-(methyl-$d_3$)-1,6-dihydropyridine-3-carboxamide (80 mg, 0.169 mmol) in anhydrous THF (2.5 mL) at 0° C., was added DIPEA (0.059 mL, 0.338 mmol) followed by 4-(((bis(benzyloxy)phosphoryl)oxy)methyl)benzoic acid (104 mg, 0.253 mmol). The reaction mixture was stirred for 2 h at 0° C. The reaction mixture was diluted with water (10 mL) and extracted with ethyl acetate (2×25 mL). The organic layer was washed with $H_2O$ (1×10 mL) and saturated NaCl (1×10 mL), dried over anhydrous $Na_2SO_4$, filtered and concentrated under reduced pressure. The crude compound was purified in reverse phase prep-HPLC (Preparative column: X-bridge phenyl (250×19 mm; 5 micron), mobile phase A: 10 mM ammonium acetate in water, mobile phase B: acetonitrile, flow rate: 18 mL/min, gradient: 0/30, 10/67). The prep fraction containing the desired product was concentrated under high vacuum at 30° C. The residue was dissolved in a mixture of acetonitrile and water and the solution was lyophilized for 24 h to afford the title compound (30 mg, 0.034 mmol, 20.08% yield) as an off-white solid. LC-MS (ES): m/z=850.4 $[M+H]^+$ Step 2

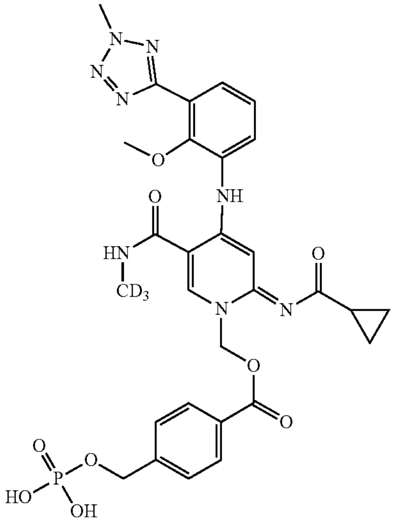

(E)-(2-((Cyclopropanecarbonyl)imino)-4-((2-methoxy-3-(2-methyl-2H-tetrazol-5-yl)phenyl)amino)-5-(methylcarbamoyl)pyridin-1(2H)-yl)methyl 4-((phosphonooxy)methyl)benzoate To a stirred solution of (E)-(2-((Cyclopropanecarbonyl)imino)-4-((2-methoxy-3-(2-methyl-2H-tetrazol-5-yl)phenyl)amino)-5-((methyl-$d_3$)carbamoyl)pyridin-1 (2H)-yl) methyl 4-(((bis(benzyloxy)phosphoryl)oxy)methyl) benzoate (30 mg, 0.035 mmol) in anhydrous DCE (2.5 mL), were added anisole (0.1 mL, 0.915 mmol) and then TFA (0.2 mL, 2.60 mmol) at room temperature. The reaction mixture was heated to 50° C. and stirred for 16 h. The reaction mixture was concentrated to dryness under high vacuum. The crude compound was purified in reverse phase prep-HPLC using formic acid as buffer. The prep fraction containing the desired product was concentrated under high vacuum at 30° C. The residue was dissolved in a mixture of acetonitrile and water and the solution was lyophilized for 24 h to afford the title compound (10 mg, 0.015 mmol, 41.5% yield) as an off-white solid. $^1H$ NMR (400 MHz, DMSO-$d_6$) δ 0.62-0.82 (m, 4H), 1.65-1.75 (m, 1H), 3.75 (s, 3H), 4.46 (s, 3H), 4.98 (d, J=7.53 Hz, 2H), 6.33 (br. s, 2H), 7.28 (s, 1H), 7.41 (d, J=8.03 Hz, 1H), 7.55 (d, J=8.03 Hz, 2H), 7.77 (br. s, 2H), 7.99 (d, J=8.03 Hz, 2H), 8.85 (br. s, 2H), 11.05 (br. s, 1H); LC-MS (ES): m/z=670.2 $[M+H]^+$; HPLC RT and purity: 11.080 min and 98.35% (method A) δ 11.919 min and 98.66% (method B).

Example 14

TABLE 1

| | 5 mpk* | | 25 mpk* | | 150 mpk* | |
|---|---|---|---|---|---|---|
| Parameter | Compound I | Example 1 | Compound I | Example 1 | Compound I | Example 1 |
| Cmax (uM) | 4.91 ± 1.4 | NA | 13 ± 1.4 | NA | 58.2 ± 5.7 | 0.69 ± 0.24 |
| Tmax (h) | 0.5 | NA | 3 | NA | 3 | 0.25 |
| AUC (uM*h) | 19.2 ± 1.7 | NA | 96.9 ± 13.2 | NA | 804.3 ± 26.9 | 0.33 ± 0.21 |
| AUC Multiple+ | 11X | | 57X | | 473X | |

As shown above in Table 1, the compound of Example 1 was dosed PO to rats to determine whether there was any circulating prodrug following administration. It was found that at therapeutic doses (5 and 25 mpk), that no exposure to the prodrug was seen. It was also shown that less than 0.05% of the prodrug was seen at the 150 mpk dose. Thus, this shows that the prodrug converts to the parent drug in vivo.

We claim:

1. A compound selected from the group consisting of:

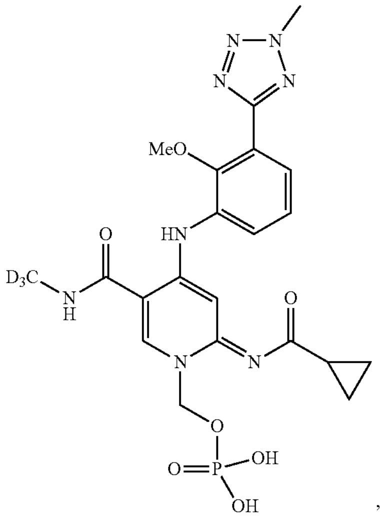

,

-continued

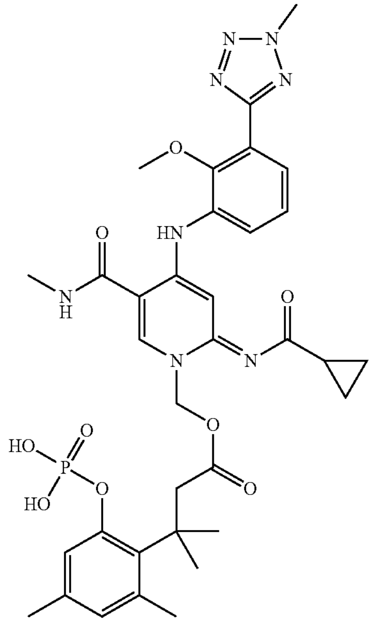

,

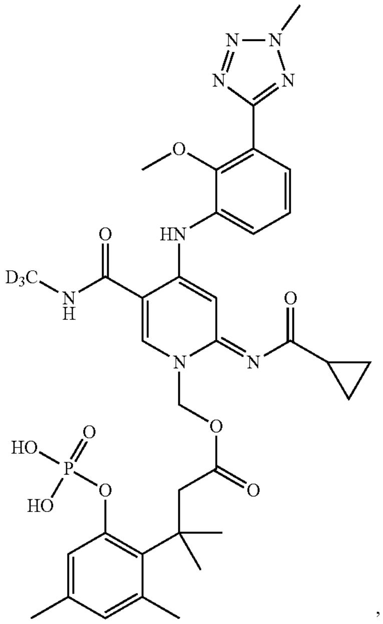

,

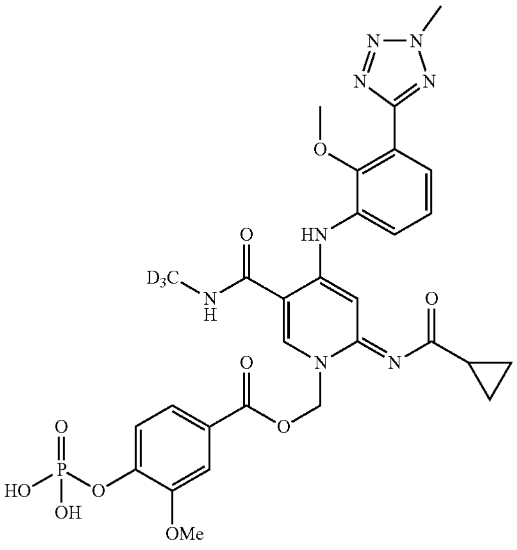
,
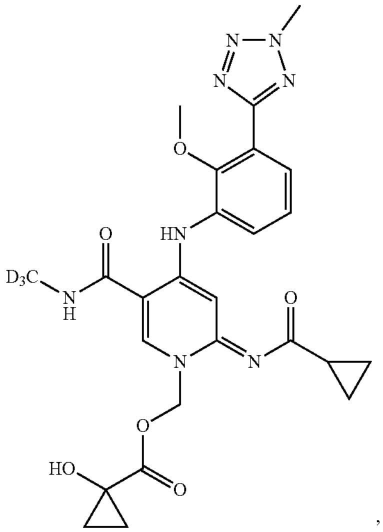
,
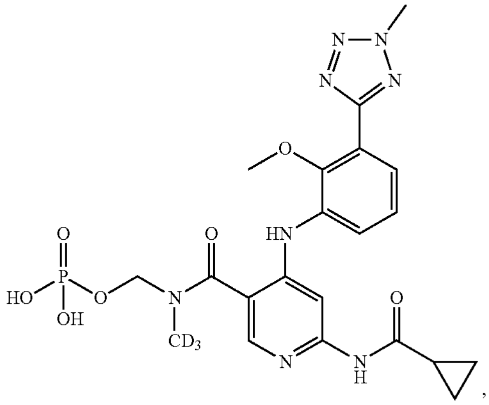
,
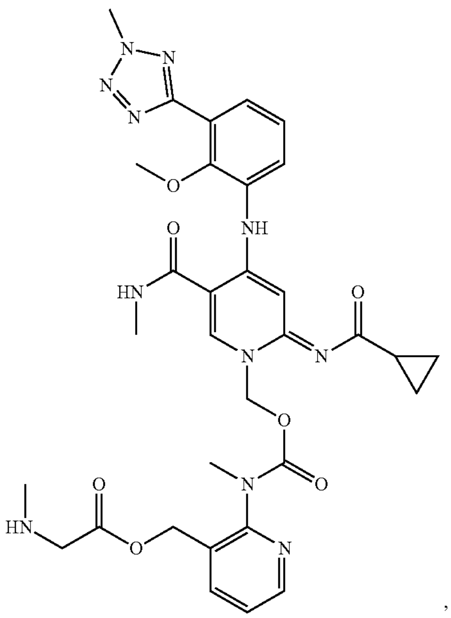
,
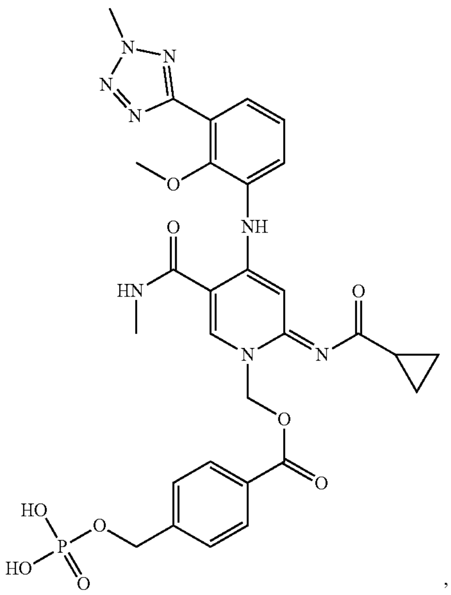
,

-continued
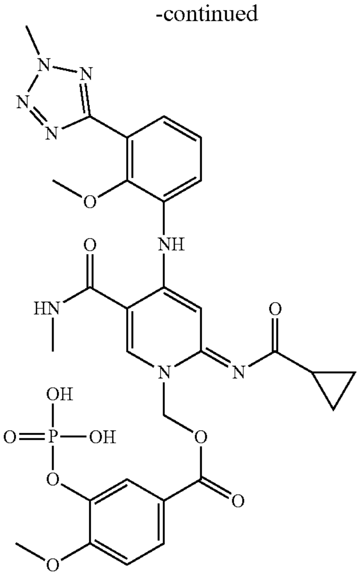
, and
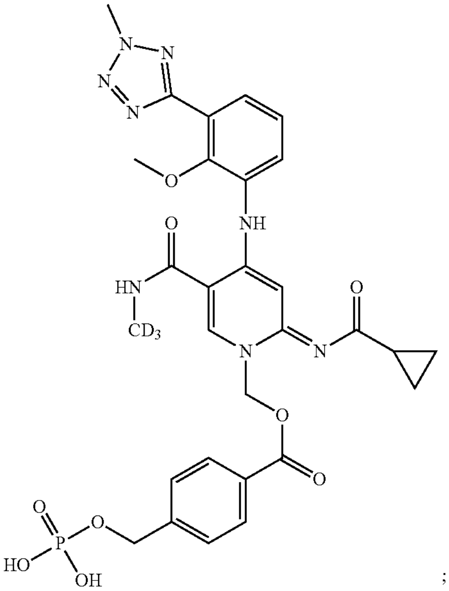 [SMILES: [2H]C([2H])([2H])NC(=O)c1cn(COC(=O)c2ccc(COP(=O)(O)O)cc2)/c(=N/C(=O)C2CC2)cc1Nc1cccc(-c2nnn(C)n2)c1OC]
;
or a salt thereof.
2. The compound of claim 1, which is selected from:
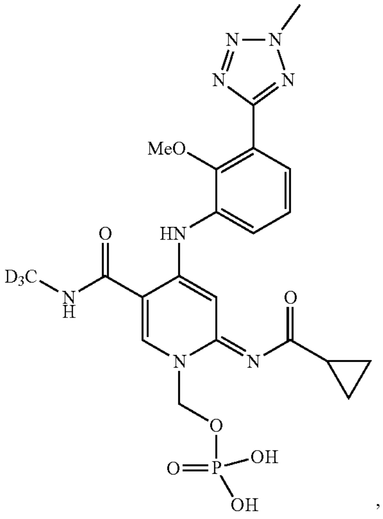
,
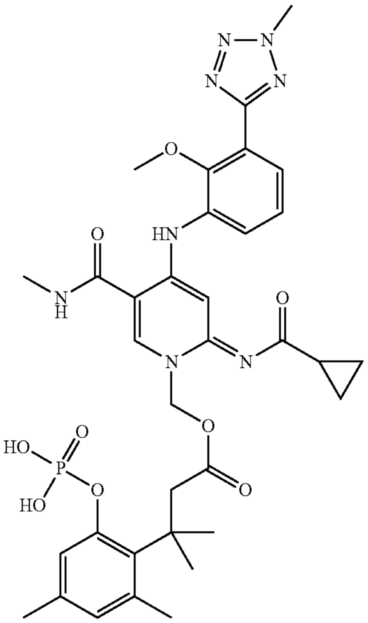
, -continued
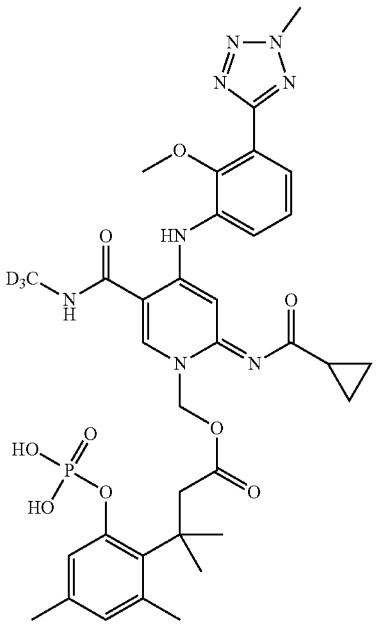
,
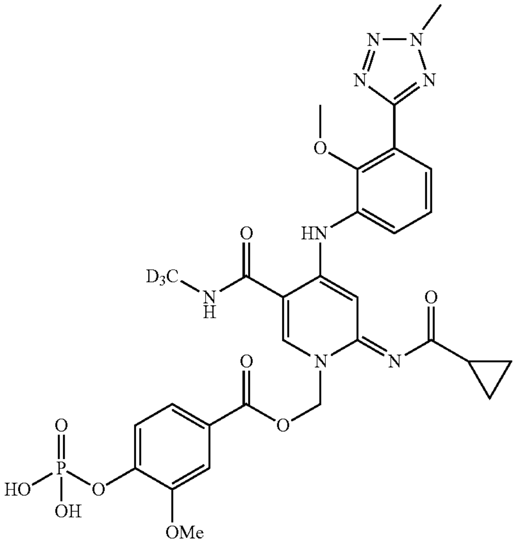
,
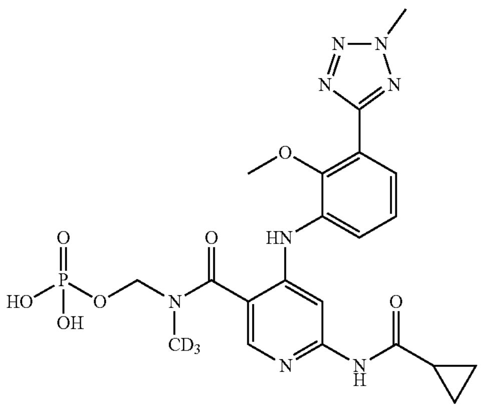
,
-continued
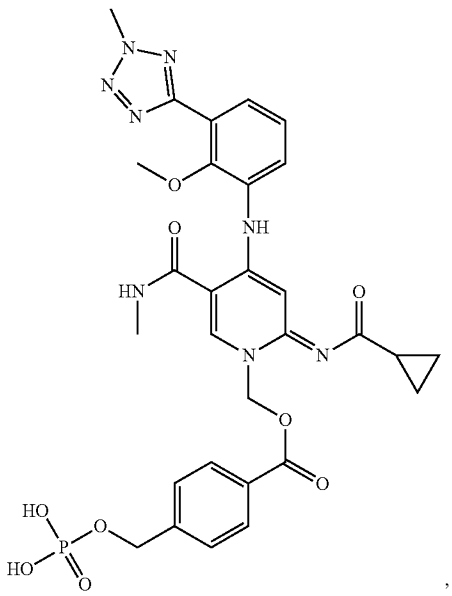
,
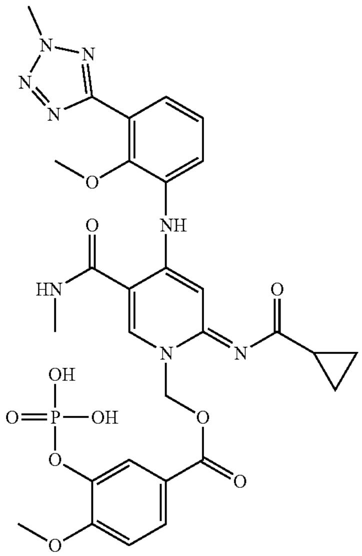
, and -continued

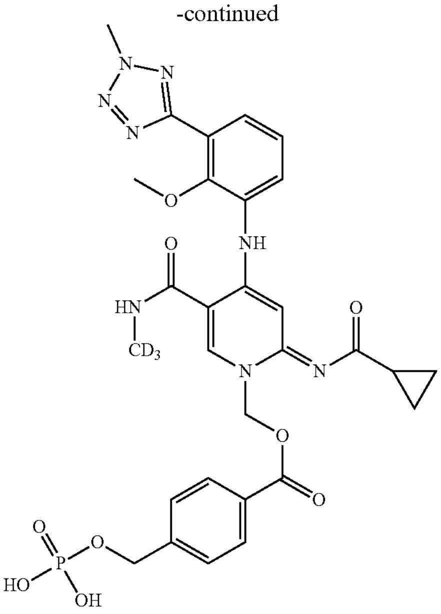
;

or a salt thereof.

3. A pharmaceutical composition comprising one or more compounds according to claim 1 and a pharmaceutically acceptable carrier or diluent.

4. A pharmaceutical composition comprising one or more compounds according to claim 2 and a pharmaceutically acceptable carrier or diluent.

5. A compound selected from the group consisting of:

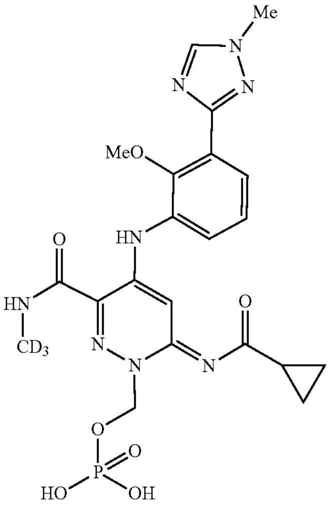
,

-continued

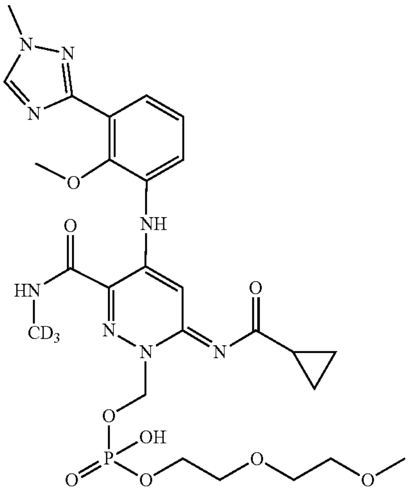
, and

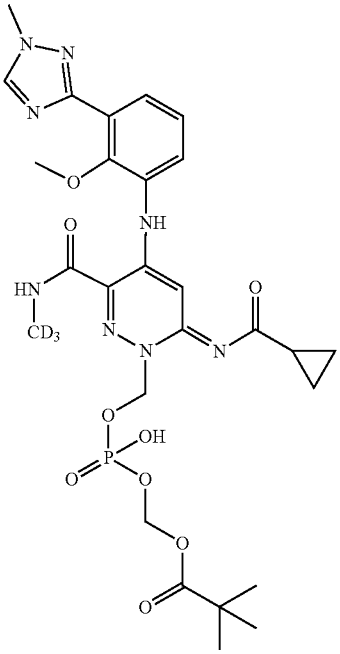
;

or a salt thereof.

6. A pharmaceutical composition comprising one or more compounds according to claim 5 and a pharmaceutically acceptable carrier or diluent.

* * * * *